US011529423B2

(12) United States Patent
Tsubusaki et al.

(10) Patent No.: US 11,529,423 B2
(45) Date of Patent: *Dec. 20, 2022

(54) BIODEGRADABLE POLYETHYLENE GLYCOL DERIVATIVE HAVING CYCLIC BENZYLIDENE ACETAL LINKER

(71) Applicant: NOF CORPORATION, Tokyo (JP)

(72) Inventors: Takuma Tsubusaki, Kawasaki (JP); Yuji Yamamoto, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 109 days.

This patent is subject to a terminal disclaimer.

(21) Appl. No.: 16/886,056

(22) Filed: May 28, 2020

(65) Prior Publication Data

US 2020/0289656 A1  Sep. 17, 2020

Related U.S. Application Data

(63) Continuation of application No. 15/563,346, filed as application No. PCT/JP2016/060377 on Mar. 30, 2016, now abandoned.

(30) Foreign Application Priority Data

Mar. 31, 2015  (JP) ................................ 2015-070659

(51) Int. Cl.
*A61K 47/60* (2017.01)
*C08G 65/333* (2006.01)

(52) U.S. Cl.
CPC ............ *A61K 47/60* (2017.08); *C08G 65/333* (2013.01); *C08G 65/33337* (2013.01); *C08G 65/33341* (2013.01)

(58) Field of Classification Search
CPC ...... A61K 47/60; A61K 47/34; C08G 65/333; C08G 65/33337; C08G 65/33341
See application file for complete search history.

(56) References Cited

U.S. PATENT DOCUMENTS

| 2008/0299069 A1 | 12/2008 | McManus et al. |
| 2013/0224870 A1 | 8/2013 | Vigh et al. |
| 2014/0039167 A1 | 2/2014 | McManus et al. |
| 2016/0046763 A1 | 2/2016 | Tsubusaki et al. |
| 2018/0298143 A1 | 10/2018 | Tsubusaki et al. |

FOREIGN PATENT DOCUMENTS

| EP | 3130587 A1 | 2/2017 |
| JP | 2014208794 A | 11/2014 |
| WO | 2005108463 A2 | 11/2005 |
| WO | 2012/027717 A2 | 3/2012 |
| WO | 2014157150 A1 | 10/2014 |
| WO | 2015152182 A1 | 10/2015 |

OTHER PUBLICATIONS

Chen, Wei et al., "pH-Responsive Biodegradable Micelles Based on Acid-Labile Polycarbonate Hydrophobe: Synthesis and Triggered Drug Release", Biomacromolecules, 2009, 10(7), pp. 1727-1735.
Extended European Search Report dated Oct. 26, 2018 issued by the European Patent Office in Corresponding European Application No. 16772952.4.
Gillies, Elizabeth R. et al., "pH-responsive copolymer assemblies for controlled release of doxorubicin", Bioconjugate Chemistry, 2005, vol. 16, No. 2, pp. 361-368.
Huang, X. et al., "pH-labile sheddable block copolymers by RAFT polymerization: Synthesis and potential use as siRNA conjugates", European Polymer Journal, 2013, 49(10), pp. 2895-2905.
Sedlak, Milos et al., "Synthesis of pH-sensitive amphotericin B-poly (ethylene glycol) conjugates and study of their controlled release in vitro", Bioorganic & Medicinal Chemistry, 2007, 15(12), pp. 4069-4076.
International Search Report dated Jul. 5, 2016, issued by the International Searching Authority in PCT/JP2016/060377 (PCT/ISA/210).
Written Opinion dated Jul. 5, 2016, issued by the International Search Authority in PCT/JP2016/060377 (PCT/ISA/237).
Vigh et al. (CAPLUS Abstract Accession No. 2012:304722 dated 2012). (Year: 2012).
Notice of Reasons for Refusal dated Apr. 9, 2020 issued by the Japanese Patent Office in Japanese Application No. 2016-065690.
Non-Final Office Action dated Jul. 18, 2018 issued by the USPTO in Parent U.S. Appl. No. 15/563,346.
Final Office Action dated Dec. 31, 2018 issued by the USPTO in Parent U.S. Appl. No. 15/563,346.
Non-Final Office Action dated Apr. 19, 2019 issued by the USPTO in Parent U.S. Appl. No. 15/563,346.
Final Office Action dated Sep. 13, 2019 issued by the USPTO in Parent U.S. Appl. No. 15/563,346.
Non-Final Office Action dated Mar. 27, 2020 issued by the USPTO in Parent U.S. Appl. No. 15/563,346.

*Primary Examiner* — Robert H Havlin
(74) *Attorney, Agent, or Firm* — Sughrue Mion, PLLC

(57) ABSTRACT

A biodegradable polyethylene glycol derivative in which a polyethylene glycol chain is linked by an acetal linker capable of accurately controlling the hydrolysis rate under different pH environments in the living body, and whose division rate into a polyethylene glycol chain of low molecular weight in the living body can be accurately controlled. The biodegradable polyethylene glycol derivative is represented by formula (1) or formula (2) as described.

21 Claims, 4 Drawing Sheets

BIODEGRADABLE POLYETHYLENE GLYCOL DERIVATIVE HAVING CYCLIC BENZYLIDENE ACETAL LINKER

CROSS REFERENCE TO RELATED APPLICATIONS

This application is a Continuation Application of U.S. application Ser. No. 15/563,346 filed Sep. 29, 2017, which is a National Stage of International Application No. PCT/JP2016/060377 filed Mar. 30, 2016, which claims priority based on Japanese Patent Application No. 2015-070659 filed Mar. 31, 2015, the contents of all of which are incorporated herein by reference in their entirety.

TECHNICAL FIELD

The present invention relates to a biodegradable polyethylene glycol derivative in which polyethylene glycol chains are linked by a hydrolysable acetal linker and which is divided in a living body into a polyethylene glycol chain of low molecular weight which can be more effectively cleared from the living body. The polyethylene glycol derivative described in the specification is used for chemical modification of a biofunctional molecule, for example, a physiologically active protein, a peptide, an antibody, a nucleic acid or a low molecular weight drug, or a drug carrier, for example, a liposome or a polymeric micelle.

BACKGROUND ART

In drug delivery system, the chemical modification of biofunctional molecule or drug carrier with polyethylene glycol, which is a hydrophilic polymer having low antigenicity, is an effective technique for increasing water solubility and bioavailability of the drug or the like and for prolonging circulation time in blood.

On the other hand, after the drug or the like connected to such a polyethylene glycol derivative is transported to the tissue or site as a target to express the efficiency, since the polyethylene glycol having a large molecular weight is insufficient in the clearance from the living body, it remains in the body for a long period of time in some cases.

As to such a problem, an approach has been made in which the polyethylene glycol chains are connected with a degradable linker and the linker is degraded in the living body, thereby dividing the polyethylene glycol chain into a polyethylene glycol chain of low molecular weight which can be more effectively cleared from the living body. Most of the strategies utilize an environment in the living body, for example, a reductive environment or an act of degrading enzyme, for the degradation of the linker, and one of them is a technique of utilizing pH in the living body.

Under pH environment in the living body, for the purpose of dividing the polyethylene glycol chain into a polyethylene glycol chain of low molecular weight which can be more effectively cleared from the living body, synthesis examples of polyethylene glycol derivative of division type in which the polyethylene glycol chains are linked by a hydrolyzable acetal linker have been reported.

For example, in Paten Document 1, a plurality of polyethylene glycol derivatives in which two polyethylene glycol chains are connected through an acetal group derived from various aldehydes or ketones are disclosed. In Paten Document 1, there is a disclosure that since the acetal group is hydrolyzed in the living body so that the polyethylene glycol chain is divided into two polyethylene glycol chains of low molecular weight, the rate of clearance from the living body is improved. However, evaluation data of hydrolysis rate of the acetal group is not shown at all and also, there is no description on the relevance between the structure around the acetal group and the hydrolysis rate.

As described above, although there are examples of polyethylene glycol derivatives in which the polyethylene glycol chains are linked by a hydrolysable acetal linker, there is no example relating to a polyethylene glycol derivative in which the hydrolysis rate of the acetal linker, that is, the division rate of the polyethylene glycol chain is accurately controlled.

PRIOR ART DOCUMENT

Patent Document

Patent Document 1: WO2005/108463

DISCLOSURE OF THE INVENTION

Problems that the Invention is to Solve

Although pH in the living body varies depending on the site, the deviation of pH at each site is small. For example, the periphery of a tumor tissue is an acidic environment in comparison with pH 7.4 in normal physiological environment, but is weakly acidic at pH of 6.4 to 6.9. Also, the endosome interior and lysosome interior in the cell have a lower pH, but are at pH of 5.5 to 6.0 and at pH of 4.5 to 5.0, respectively, so that the deviation of pH is small. Therefore, in order to connect a polyethylene glycol derivative in which polyethylene glycol chains are linked by an acetal linker with a drug or the like and after expressing the efficiency under different pH environments in the living body, to divide the polyethylene glycol chain into a polyethylene glycol chain of low molecular weight in each of these sites, it is necessary to accurately control the hydrolysis rate of the acetal linker under different pH environments in the living body.

An object of the present invention is to provide a biodegradable polyethylene glycol derivative in which polyethylene glycol chains are linked by an acetal linker capable of accurately controlling the hydrolysis rate under different pH environments in the living body, and whose division rate into a polyethylene glycol chain of low molecular weight in the living body can be accurately controlled.

Means for Solving the Problems

As a result of the intensive investigations to solve the problem described above, the inventors have developed a biodegradable polyethylene glycol derivative in which polyethylene glycol chains are linked by a cyclic benzylidene acetal linker capable of accurately controlling the hydrolysis rate under different pH environments in the living body, and whose division rate into a polyethylene glycol chain of low molecular weight in the living body can be accurately controlled.

The feature of the invention resides in that a plurality of polyethylene glycol chains are connected through a cyclic benzylidene acetal linker having substituent(s). By appropriately selecting the kind and position of the substituent(s) on the benzene ring of the cyclic benzylidene acetal linker, the degrees of electron density and steric hindrance around the acetal group which affect the hydrolysis rate of the acetal linker can be adjusted. Based on the feature, it is possible to impart a desired hydrolysis rate to the acetal linker and after the drug or the like connected to the biodegradable polyethylene glycol derivative is transported to the tissue or site as a target to express the efficiency, it is possible to divide the polyethylene glycol chain into a polyethylene glycol chain of low molecular weight at an arbitrary rate under pH environment in each of these sites.

That is, the invention includes the following items.

[1] A biodegradable polyethylene glycol derivative having a cyclic benzylidene acetal linker represented by formula (1) or formula (2) shown below:

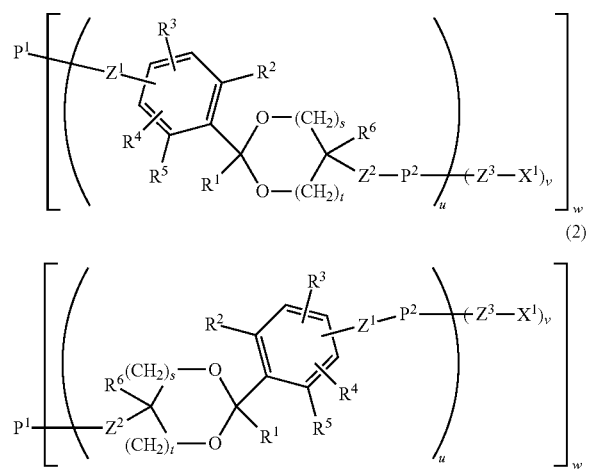

in formula (1) and formula (2), $R^1$ and $R^6$ are each independently a hydrogen atom or a hydrocarbon group; $R^2$, $R^3$, $R^4$ and $R^5$ are each independently an electron-withdrawing or electron-donating substituent or a hydrogen atom; s is 1 or 2, t is 0 or 1, and s+t is 1 or 2; $P^1$ is a straight-chain or branched polyethylene glycol having a number of ethylene glycol units of 3 or more; $P^2$ is a straight-chain or branched polyethylene glycol having a number of ethylene glycol units of 3 or more; w is a valence of $P^1$ connected to a cyclic benzylidene acetal and is an integer of 1 to 8; u is a number of a structural unit composed of the cyclic benzylidene acetal and $P^2$ which are connected each other in series and is an integer of 1 to 40; v is a number of $X^1$ connected to $P^2$ and is an integer of 1 to 4; $X^1$ is a chemically reactive functional group; and $Z^1$, $Z^2$ and $Z^3$ are each independently a selected divalent spacer.

[2] The biodegradable polyethylene glycol derivative of [1], wherein s is 1 and t is 0, $R^2$ and $R^5$ are each a hydrogen atom, and a sum ($\Sigma\sigma$) of substituent constants ($\sigma$) in $R^3$, $R^4$ and $P^1$—$Z^1$ in formula (1) or in $R^3$, $R^4$ and $P^2$—$Z^1$ in formula (2) satisfies $-0.30 \leq \Sigma\sigma \leq 1.05$.

[3] The biodegradable polyethylene glycol derivative of [1], wherein s is 1 and t is 0, at least one of $R^2$ and $R^5$ is the substituent described above, and a sum ($\Sigma\sigma$) of substituent constants ($\sigma$) in $R^3$, $R^4$ and $P^1$—$Z^1$ in formula (1) or in $R^3$, $R^4$ and $P^2$—$Z^1$ in formula (2) satisfies $-1.71 \leq \Sigma\sigma \leq 0.88$.

[4] The biodegradable polyethylene glycol derivative of [1], wherein s is 1 and t is 1, or s is 2 and t is 0, $R^2$ and $R^5$ are each a hydrogen atom, and a sum ($\Sigma\sigma$) of substituent constants ($\sigma$) in $R^3$, $R^4$ and $P^1$—$Z^1$ in formula (1) or in $R^3$, $R^4$ and $P^2$—$Z^1$ in formula (2) satisfies $-0.19 \leq \Sigma\sigma \leq 0.57$.

[5] The biodegradable polyethylene glycol derivative of [1], wherein s is 1 and t is 1, or s is 2 and t is 0, at least one of $R^2$ and $R^5$ is the substituent described above, and a sum ($\Sigma\sigma$) of substituent constants ($\sigma$) in $R^3$, $R^4$ and $P^1$—$Z^1$ in formula (1) or in $R^3$, $R^4$ and $P^2$—$Z^1$ in formula (2) satisfies $-0.98 \leq \Sigma\sigma \leq 0.48$.

[6] The biodegradable polyethylene glycol derivative of any one of [1] to [5], wherein w is 1.

[7] The biodegradable polyethylene glycol derivative of [6], wherein $P^1$ is a straight-chain polyethylene glycol having a hydrocarbon group or a chemically reactive functional group at a terminal thereof.

[8] The biodegradable polyethylene glycol derivative of [7], wherein $P^1$ is represented by formula (3):

in the formula (3), Y is a hydrocarbon group having from 1 to 24 carbon atoms; and n is an integer of 3 to 2,000.

[9] The biodegradable polyethylene glycol derivative of [7], wherein $P^1$ is represented by formula (4):

in the formula (4), $X^2$ is a chemically reactive functional group different from $X^1$; $Z^4$ is a divalent spacer; and n is an integer of 3 to 2,000.

[10] The biodegradable polyethylene glycol derivative of [6], wherein $P^1$ is a branched polyethylene glycol having a hydrocarbon group or a chemically reactive functional group different from $X^1$ at a terminal thereof.

[11] The biodegradable polyethylene glycol derivative of [10], wherein $P^1$ is represented by formula (5):

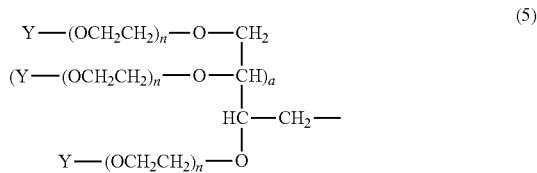

in the formula (5), Y is a hydrocarbon group having from 1 to 24 carbon atoms; n is an integer of 3 to 1,000; and a is 0 or 2.

[12] The biodegradable polyethylene glycol derivative of [10], wherein $P^1$ is represented by formula (6):

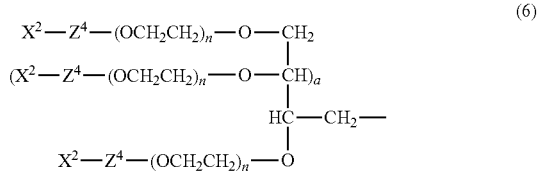

in the formula (6), $X^2$ is a chemically reactive functional group different from $X^1$; $Z^4$ is a divalent spacer; n is an integer of 3 to 1,000, and a is 0 or 2.

[13] The biodegradable polyethylene glycol derivative of any one of [1] to [5], wherein w is 2 to 8.

[14] The biodegradable polyethylene glycol derivative of [13], wherein $P^1$ is represented by formula (7):

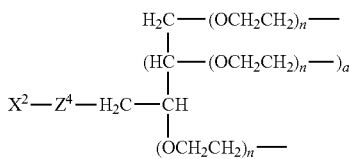
(7)

in the formula (7), $X^2$ is a chemically reactive functional group different from $X^1$; $Z^4$ is a divalent spacer; n is an integer of 3 to 1,000, and a is 0 or 2.

[15] The biodegradable polyethylene glycol derivative of [13], wherein $P^1$ is a straight-chain polyethylene glycol or a branched polyethylene glycol having a number of terminals of 3 to 8, all terminals of the polyethylene glycol constituting $P^1$ are each connected to $Z^1$ in formula (1) or $Z^2$ in formula (2), and w is equal to the number of terminals of the polyethylene glycol.

[16] The biodegradable polyethylene glycol derivative of [15], wherein $P^1$ is selected from the group consisting of formula (r), formula (s), formula (t), formula (u) and formula (v):

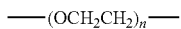
(r)

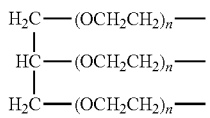
(s)

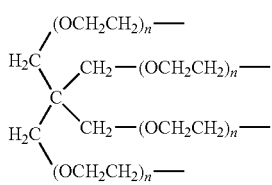
(t)

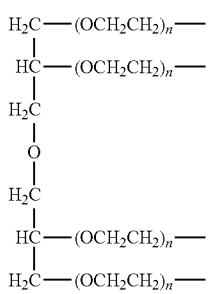
(u)

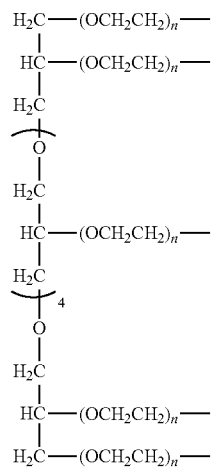
(v)

in the formulae, n is an integer of 3 to 2,000; and w is 2 in a case where $P^1$ is represented by formula (r), w is 3 in a case where $P^1$ is represented by formula (s), w is 4 in a case where $P^1$ is represented by formula (t), w is 4 in a case where $P^1$ is represented by formula (u), and w is 8 in a case where $P^1$ is represented by formula (v).

[17] The biodegradable polyethylene glycol derivative of any one of [1] to [16], wherein $P^2$ is represented by formula (8):

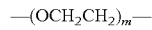
(8)

in the formula (8), m is an integer of 3 to 2,000; and v in formula (1) or formula (2) is 1.

[18] The biodegradable polyethylene glycol derivative of any one of [1] to [16], wherein $P^2$ is represented by formula (9):

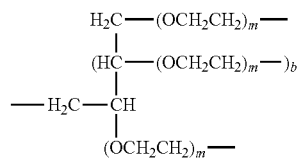
(9)

in the formula (9), m is an integer of 3 to 1,000, b is 0 or 2; and v in formula (1) or formula (2) is b+2.

[19] The biodegradable polyethylene glycol derivative of any one of [1] to [18], wherein $X^1$ is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

[20] The biodegradable polyethylene glycol derivative of any one of [1] to [19], wherein $Z^1$, $Z^2$ and $Z^3$ are each independently an ether bond, an ester bond, a carbonate bond, a urethane bond, an amide bond, a secondary amino group, an alkylene group containing any of these bonds and group, a single bond or an alkylene group.

[21] The biodegradable polyethylene glycol derivative of [9], [12] or [14], wherein $X^2$ is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

[22] The biodegradable polyethylene glycol derivative of [9], [12] or [14], wherein $Z^4$ is an ether bond, an ester bond, a carbonate bond, a urethane bond, an amide bond, a secondary amino group, an alkylene group containing any of these bonds and group, a single bond or an alkylene group.

Advantage of the Invention

In the biodegradable polyethylene glycol derivative having a cyclic benzylidene acetal linker according to the invention, the hydrolysis rate of the cyclic benzylidene acetal linker can be adjusted under different pH environments in the living body. Therefore, after the drug or the like connected to the biodegradable polyethylene glycol derivative is transported to the tissue or site as a target to express the efficiency, it is possible to divide the polyethylene glycol chain into a polyethylene glycol chain of low molecular weight at an arbitrary rate under pH environment in each of these sites. Thus, the problem, which is a disadvantage in conventional polyethylene glycol modification, in that since the polyethylene glycol having a large molecular weight is insufficient in the clearance from the living body, it remains in the body for a long period of time, can be fundamentally eliminated. That is, by using the biodegradable polyethylene glycol derivative in the chemical modification of the drug or the like, it is able to impart not only the advantages of polyethylene glycol modification, for example, an increase in water solubility and bioavailability and prolongation of circulation time in blood, but also the advantage in that after the drug or the like expresses the efficiency, the clearance of the polyethylene glycol from the living body is excellent.

MODE FOR CARRYING OUT THE INVENTION

Figure 1:
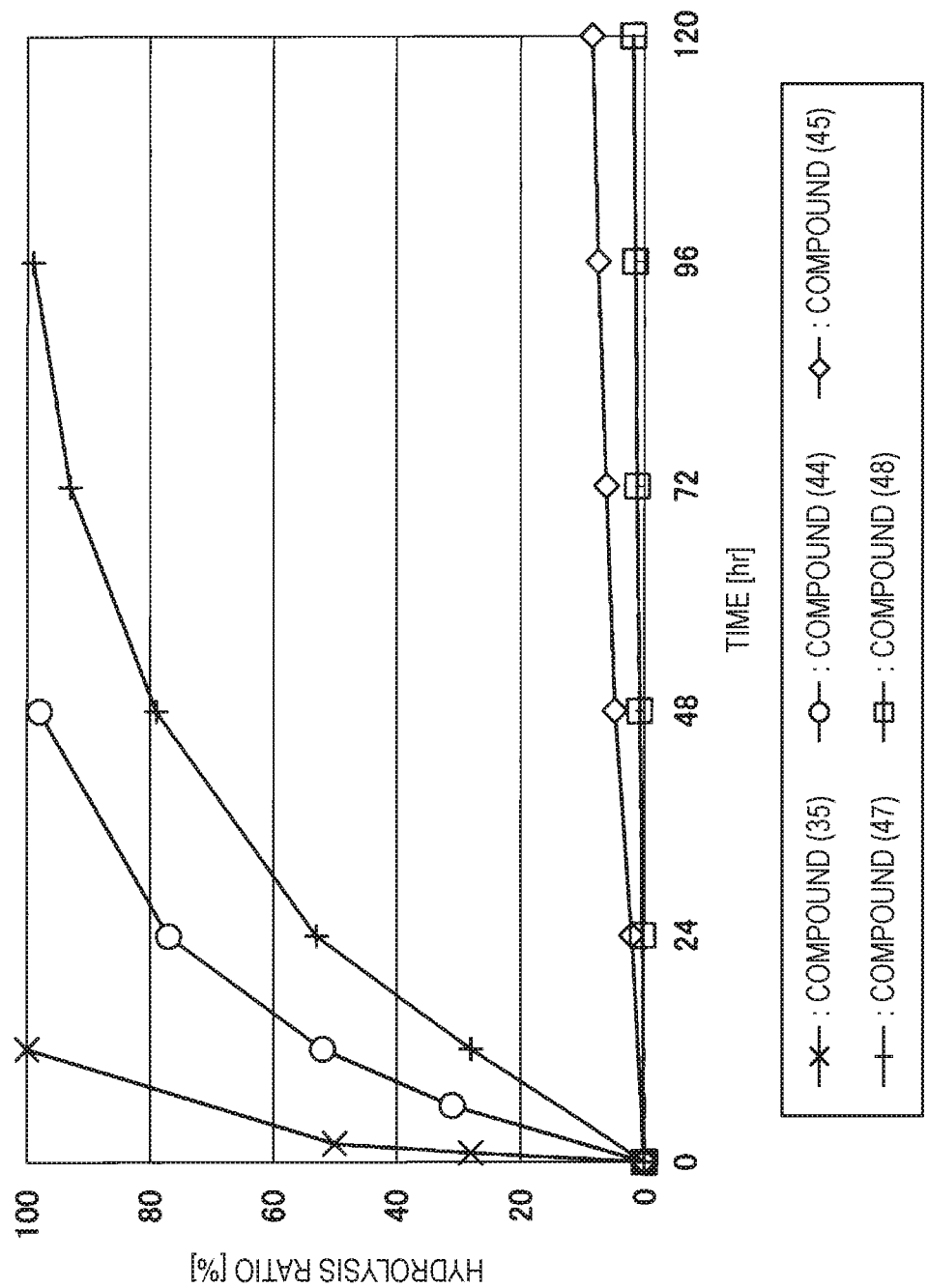
FIG. 1 shows results of the hydrolysis test in MES deuterated water buffer of pD 5.5 at 37° C. using the compounds of formula (35), formula (44), formula (45), formula (47) and formula (48) described in Examples.

The invention will be described in detail hereinafter.

The term "acetal" as used in the specification means both of an acetal structure derived from an aldehyde and an acetal structure derived from a ketone, that is, a ketal structure.

The term "cyclic acetal" as used in the invention means both of a 1,3-dioxolane structure of a 5-membered ring which is s is 1 and t is 0 in formula (1) or formula (2) and a 1,3-dioxane structure of a 6-membered ring which is s is 1 and t is 1 or s is 2 and t is 0 in formula (1) or formula (2).

Each of $R^1$ and $R^6$ in formula (1) or formula (2) of the invention is a hydrogen atom or a hydrocarbon group, and a number of carbon atoms of the hydrocarbon group is preferably 10 or less and more preferably 4 or less. Specific examples of the hydrocarbon group include a methyl group, an ethyl group, a propyl group, an isopropyl group, a tert-butyl group, a phenyl group and a benzyl group. A preferred embodiment of $R^1$ is a hydrogen atom or a methyl group, and a hydrogen atom is more preferred.

The benzene ring in formula (1) or formula (2) of the invention may have a plurality of substituents. By appropriately selecting the kind, the position and the degree of electron-donating property and electron-withdrawing property of the substituents on the benzene ring, it is possible to adjust the degrees of electron density and steric hindrance around the acetal group which affects the hydrolysis rate of the cyclic acetal linker. This makes it possible to impart a desired hydrolysis rate to the cyclic acetal linker.

In the specification, the substituent(s) on the benzene ring in formula (1) or formula (2) is described using the "substituent constant (σ)" which means the substituent constant in the Hammett's rule which quantifies the effect of the substituent on the reaction rate or equilibrium of benzene derivative. However, as is known, the Hammett's rule is applied only to a para-substituted or meta-substituted benzene derivative and cannot be applied to an ortho-substituted benzene derivative which is affected by steric hindrance. Therefore, in the case of ortho-substituted benzene derivative, the substituent constant means the substituent constant in the Taft's equation which extends the Hammett's rule described above.

In the para-substituted or meta-substituted benzene derivative described above, the Hammett's rule is represented by equation (10) shown below.

$$\log(k/k_0)=\rho\sigma \qquad (10)$$

in the equation, k is a rate constant or equilibrium constant in an arbitrary reaction of para-substituted or meta-substituted benzene derivative, $k_0$ is a rate constant or equilibrium constant in the case where the benzene derivative does not have the substituent, that is, the substituent is a hydrogen atom, ρ is a reaction constant, and σ is a substituent constant.

The reaction constant (ρ) in equation (10) described above is a constant which is determined depending on reaction conditions, for example, kind, temperature or solvent of the reaction, and can be calculated from the slope of Hammett plots. In the acid hydrolysis reaction of the hydrophilic polymer derivative having a cyclic benzylidene acetal linker of the invention, in the case of 1,3-dioxolane structure, the constant is calculated as "ρ=−2.7" from the results of the hydrolysis tests performed for the compounds of formula (35), formula (44) and formula (45). Also, in the case of 1,3-dioxane structure, the constant is calculated as "ρ=−4.8" from the results of the hydrolysis tests performed for the compounds of formula (47) and formula (48).

The substituent constant (σ) in equation (10) described above is a constant which is determined only depending on the kind and position of the substituent, regardless of the kind of reaction, and in the case where no substituent is present, that is, the substituent is a hydrogen atom, the constant is "0". The term "electron-withdrawing" as used in the specification means the case where σ is a positive value and the term "electron-donating" means the case where σ is a negative value.

As described above, the Hammett's rule is applied only to a para-substituted or meta-substituted benzene derivative and cannot be applied to the case of an ortho-substituted benzene derivative which is affected by steric hindrance. Therefore, it is the Taft's equation that the effect of such steric hindrance is introduced as a factor of the position, that is, a position constant (Es) of the substituent, to extend the Hammett's rule so that it can also be applied to the case of the ortho-substituted benzene derivative. The Taft's equation is represented by equation (11) shown below.

$$\log(k/k_0)=\rho^*\sigma^*+Es \quad (11)$$

in the equation, k is a rate constant or equilibrium constant in an arbitrary reaction of para-substituted or meta-substituted benzene derivative, $k_0$ is a rate constant or equilibrium constant in the case where the benzene derivative does not have a substituent, that is, the substituent is a hydrogen atom, $\rho^*$ is a reaction constant, $\sigma^*$ is a substituent constant, and Es is a position constant of the substituent.

As is known, since the reaction constant ($\rho$) of para-substituted or meta-substituted benzene derivative and the reaction constant ($\rho^*$) of ortho-substituted benzene derivative are approximately equal, it is defined in the specification that $\rho$ and $\rho^*$ are the same. Since the substituent constant ($\sigma^*$) in the ortho position is similar to the substituent constant in the para position as described, for example, in "Charton, M. Can. J. Chem. 1960, 38, 2493-2499", to the substituent constant in the ortho position in the specification is applied a corresponding substituent constant in the para position.

The substituent constant ($\sigma$) in the para position or the meta position is described in "Hansch, C.; Leo, A.; Taft, R. W. Chem. Rev. 1991, 91, 165-195", and with respect to a substituent in which the substituent constant ($\sigma$) is unknown, the constant can be measured and determined by the method described in "Hammett, L. P. Chem. Rev. 1935, 17(1), 125-136". Moreover, the position constant (Es) is described in "Unger, S. H.; Hansch, C. Prog. Phys. Org. Chem. 1976, 12, 91-118". However, as to Es as used in the specification, a hydrogen atom is defined as "0".

In formula (1) or formula (2), in the case where a plurality of substituents are present on the benzene ring, it is defined that additivity is established for the substituent constant ($\sigma$) and the position constant (Es) thereof, and the sum of $\sigma$ is represented by "$\Sigma\sigma$" and the sum of Es is represented by "$\Sigma$Es".

$Z^1$ is connected to the benzene ring of the cyclic benzylidene acetal and $P^1$—$Z^1$ or $P^2$—$Z^1$ is also a substituent of the benzene ring. The substituent constant of $P$—$Z^1$ or $P^2$—$Z^1$ can be determined by separately measuring as to the combination of $P^1$ and $Z^1$ or the combination of $P^2$ and $Z^1$, but, since the substituent constant of $P^1$—$Z^1$ or $P^2$—$Z^1$ is substantially affected largely by the structure in the vicinity of the connecting portion to the benzene ring, the effect of the other portions is so small as to be ignored. Therefore, it is possible to use a known substituent constant of a structure similar to the structure in the vicinity of the connecting portion to the benzene ring in place of separately measuring the substituent constant as to $P^1$—$Z^1$ or $P^2$—$Z^1$.

It is defined that the substituent constant of $P^1$—$Z^1$ or $P^2$—$Z^1$ in the specification can be substituted with a substituent constant of a structure in which atom(s) other than the second atom connected to the third atom counted from the atom connected to the benzene ring in the backbone atoms of the main chain of $P^1$—$Z^1$ or $P^2$—$Z^1$ are substituted with hydrogen atom(s). However, in the case where, when the atom is substituted with a hydrogen atom, a carboxy group is formed, it is defined that the substituent constant of $P^1$—$Z^1$ or $P^2$—$Z^1$ can be substituted with a substituent constant of a structure in which the atom is substituted with a methyl group in place of a hydrogen atom.

Specific examples of the structure of the connecting portion to the benzene ring in $P^1$—$Z^1$ or $P^2$—$Z^1$ and the structure for the substitution are shown below. In the case of (r1) shown below, wherein the connecting portion to the benzene ring in $P^1$—$Z^1$ or $P^2$—$Z^1$ is an ether bond, a substituent constant of (r2) shown below is applied. In the cases of (r3) and (r5) shown below, wherein the connecting portion to the benzene ring in $P^1$—$Z^1$ or $P^2$—$Z^1$ is an amide bond, substituent constants of (r4) and (r6) shown below are applied, respectively. In the case of (r7) shown below, wherein the connecting portion to the benzene ring in $P^1$—$Z^1$ or $P^2$—$Z^1$ is a urethane bond, a substituent constant of (r8) shown below is applied.

| | Structure of Connecting Portion to Benzene Ring | | Structure for Substitution |
|---|---|---|---|
| (r1) | —CH$_2$CH$_2$O—⟨Ph⟩ | (r2) | H—CH$_2$CH$_2$O—⟨Ph⟩ |
| (r3) | —CH$_2$C(=O)N(H)—⟨Ph⟩ | (r4) | H—CH$_2$C(=O)N(H)—⟨Ph⟩ |
| (r5) | —CH$_2$N(H)C(=O)—⟨Ph⟩ | (r6) | H—CH$_2$N(H)C(=O)—⟨Ph⟩ |
| (r7) | —OC(=O)N(H)—⟨Ph⟩ | (r8) | CH$_3$—OC(=O)N(H)—⟨Ph⟩ |

As to the hydrolysis rate of the biodegradable polyethylene glycol derivative having a cyclic benzylidene acetal linker of the invention, hydrolysis half-life ($t_{1/2}$) in a buffer at pH 5.5 and 37° C. is preferably in the range from 1 hour to 6 months, more preferably in the range from 1 hour to 1 month, and still more preferably in the range from 1 hour to 24 hours. In the specification, using a numerical value derived from the compound of formula (44) described in Examples in which $t_{1/2}$ under the hydrolysis conditions described above is 12 hours, a preferred range of the sum ($\Sigma\sigma$) of substituent constants in the case where a 1,3-dioxolane structure is included is defined. When $\log(k/k_0)$ for the compound of formula (44) is calculated using equation (10) above, equation (12) shown below is obtained. However, as defined above, $P^1$—$Z^1$ in the compound of formula (44) is substituted with an ethoxy group ($CH_3CH_2$—).

$$\log(k/k_0) = -2.7 \times (0.34 - 0.24) = -0.27 \quad (12)$$

In the case where $R^2$ and $R^5$ in formula (1) or formula (2) are hydrogen atoms, when $\log(k'/k_0)$ is calculated by taking the rate constant at the time when $t_{1/2}$ is 24 hours as k' using equation (12) and equation (10) above, equation (13) shown below is obtained.

$$\log(k'/k) = \log\{(12/24)k/k\} = -0.30$$

When the equation is modified, $$\log(k'/k) = \log[(k'/k_0)/(k/k_0)] = -0.30$$

$$\log(k'/k_0) - \log(k/k_0) = -0.30$$

When equation (12) above is substituted, $$\log(k'/k_0) - (-0.27) = -0.30$$

$$\log(k'/k_0) = -0.57 \quad (13)$$

Here, when the sum ($\Sigma\sigma$) of the substituent constants is calculated using equation (13) and equation (10) above, equation (14) shown below is obtained.

$$\log(k'/k_0) = -2.7 \times \Sigma\sigma = -0.57$$

$$\Sigma\sigma = 0.21 \quad (14)$$

Similarly, in the case where $R^2$ and $R^5$ in formula (1) or formula (2) are hydrogen atoms, when $\log(k''/k_0)$ is calculated by taking the rate constant at the time when $t_{1/2}$ is 1 hour as k'', equation (15) shown below is obtained.

$$\log(k''/k) = \log(12k/k) = 1.08$$

When the equation is modified, $$\log(k''/k) = \log[(k''/k_0)/(k/k_0)] = 1.08$$

$$\log(k''/k_0) - \log(k/k_0) = 1.08$$

When equation (12) above is substituted, $$\log(k''/k_0) - (-0.27) = 1.08$$

$$\log(k''/k_0) = 0.81 \quad (15)$$

Here, when the sum ($\Sigma\sigma$) of the substituent constants is calculated using equation (15) and equation (10) above, equation (16) shown below is obtained.

$$\log(k''/k_0) = -2.7 \times \Sigma\sigma = 0.81$$

$$\Sigma\sigma = -0.30 \quad (16)$$

From equation (14) and equation (16), in the case where formula (1) or formula (2) includes a 1,3-dioxolane structure and $R^2$ and $R^5$ are hydrogen atoms, when the range of $\Sigma\sigma$ satisfies $-0.30 \leq \Sigma\sigma \leq 0.21$, $t_{1/2}$ of the biodegradable polyethylene glycol derivative is represented by 1 hour$\leq t_{1/2} \leq$24 hours. Similarly, when the ranges of $\Sigma\sigma$ at 1 hour$\leq t_{1/2} \leq$1 month and 1 hour$\leq t_{1/2} \leq$6 months are calculated, $-0.30 \leq \Sigma\sigma \leq 0.76$ at the time of 1 hour$\leq t_{1/2} \leq$1 month and $-0.30 \leq \Sigma\sigma \leq 1.05$ at the time of 1 hour$\leq t_{1/2} \leq$6 months, respectively.

The substituent which can be used in the invention is a substituent which does not inhibit the acetalization reaction of the cyclic benzylidene acetal linker compound, the coupling reaction of the cyclic benzylidene acetal linker compound with a polyethylene glycol intermediate, the terminal functional group conversion reaction of the polyethylene glycol intermediate and the linking reaction of the polyethylene glycol intermediate in the synthesis process of the biodegradable polyethylene glycol derivative, and further the bond-forming reaction between the biodegradable polyethylene glycol derivative and the drug or the like.

The substituent may be any of electron-withdrawing substituent and electron-donating substituent as far as it satisfies the conditions described above, and the substituents may be used individually or in combination. The electron-withdrawing substituent includes an acyl group having from 2 to 5 carbon atoms, an alkoxycarbonyl group having from 2 to 5 carbon atoms, a carbamoyl group having from 2 to 5 carbon atoms, an acyloxy group having from 2 to 5 carbon atoms, an acylamino group having from 2 to 5 carbon atoms, an alkoxycarbonylamino group having from 2 to 5 carbon atoms, a fluorine atom, a chlorine atom, a bromine atom, an iodine atom, an alkylsulfanyl group having from 1 to 4 carbon atoms, an alkylsulfonyl group having from 1 to 4 carbon atoms, an arylsulfonyl group having from 6 to 10 carbon atoms, a nitro group, a trifluoromethyl group and a cyano group, and preferred examples thereof include an acetyl group, a methoxycarbonyl group, a methylcarbamoyl group, an acetoxy group, an acetamide group, a methoxycarbonylamino group, a fluorine atom, a chlorine atom, a bromine atom, an iodine atom, a methylsulfanyl group, a phenylsulfonyl group, a nitro group, a trifluoromethyl group and a cyano group. The electron-donating substituent includes an alkyl group having from 1 to 4 carbon atoms, and preferred examples thereof include a methyl group, an ethyl group, a propyl group, an isopropyl group and a tert-butyl group. The substituent which is an electron-withdrawing group in the meta-position and an electron-donating group in the para-position or the ortho-position includes an alkoxy group having from 1 to 4 carbon atoms, an aryl group having from 6 to 10 carbon atom and an aryloxy group having from 6 to 10 carbon atoms, and preferred examples thereof include a methoxy group, an ethoxy group, a propoxy group, an isopropoxy group, a tert-butoxy group, a phenyl group and a phenoxy group.

In the case where formula (1) or formula (2) includes a 1,3-dioxolane structure and at least one of $R^2$ and $R^5$ is a substituent other than a hydrogen atom, using the position constants (Es) of a phenyl group which has the largest influence of steric hindrance and a fluorine atom which has the smallest influence of steric hindrance among the substituents described above, the ranges of $\Sigma\sigma$ in a buffer at pH 5.5 and 37° C. at 1 hour$\leq t_{1/2} \leq$24 hours, 1 hour$\leq t_{1/2} \leq$1 month, and 1 hour$\leq t_{1/2} \leq$6 months are calculated by using Taft's equation (11), respectively. As a result, it is found that $-1.71 \leq \Sigma\sigma \leq 0.04$ at the time of 1 hour$\leq t_{1/2} \leq$24 hours, $-1.71 \leq \Sigma\sigma \leq 0.59$ at the time of 1 hour$\leq t_{1/2} \leq$1 month, and $-1.71 \leq \Sigma\sigma \leq 0.88$ at the time of 1 hour$\leq t_{1/2} \leq$6 months, respectively.

In the case where formula (1) or formula (2) includes a 1,3-dioxolane structure and $R^2$ and $R^5$ are hydrogen atoms, for example, a preferred embodiment which satisfies $-0.30 \leq \Sigma\sigma \leq 0.21$ at the time of 1 hour$\leq t_{1/2} \leq 24$ hours is described below. However, the substituents shown herein means $R^3$ and $R^4$ and the structure used in place of $P^1$—$Z^1$ or $P^2$—$Z^1$ according to the definition described above. In the preferred embodiment, one of the meta-positions in formula (1) or formula (2) is a methoxy group, an ethoxy group or an acetamide group, and more preferably an ethoxy group or an acetamide group. In another preferred embodiment, the para-position in formula (1) or formula (2) is a methoxy group or an ethoxy group and one of the meta-positions is a substituent selected from the group consisting of a fluorine atom, a chlorine atom, a bromine atom and an iodine atom, and more preferably the para-position is an ethoxy group and one of the meta-positions is a fluorine atom or a chlorine atom. In still another preferred embodiment, one of the para-position and the meta-position in formula (1) or formula (2) is a methoxy group, an ethoxy group or an acetamide group, and more preferably a methoxy group or an ethoxy group.

Further, in the case where formula (1) or formula (2) includes a 1,3-dioxolane structure and at least one of $R^2$ and $R^5$ is a substituent other than a hydrogen atom, for example, a preferred embodiment which satisfies $-1.71 \leq \Sigma\sigma \leq 0.04$ at the time of 1 hour$\leq t_{1/2} \leq 24$ hours is described below. However, the substituents shown herein means $R^3$ and $R^4$ and the structure used in place of $P^1$—$Z^1$ or $P^2$—$Z^1$ according to the definition described above. In the case where one of $R^2$ and $R^5$ in formula (1) or formula (2) is a fluorine atom, a methyl group or an ethyl group and the other is a hydrogen atom, the para-position is preferably an ethoxy group or an acetamide group, and more preferably an ethoxy group. In the case where one of $R^2$ and $R^5$ in formula (1) or formula (2) is a methoxy group and the other is a hydrogen atom, the para-position is preferably a substituent selected from the group consisting of a methoxymethyl group and an acetamide group, and more preferably an acetamide group.

Moreover, using a numerical value derived from the compound of formula (35) described in Examples in which the hydrolysis half-life ($t_{1/2}$) in a buffer at pH 5.5 and 37° C. is 24 hours, a preferred range of the sum ($\Sigma\sigma$) of substituent constants in the case where formula (1) or formula (2) includes a 1,3-dioxane structure can be defined.

In the case where formula (1) or formula (2) includes a 1,3-dioxane structure and $R^2$ and $R^5$ are hydrogen atoms, when the range of $\Sigma\sigma$ satisfies $-0.19 \leq \Sigma\sigma \leq 0.10$, $t_{1/2}$ of the hydrophilic polymer derivative is represented by 1 hour$\leq t_{1/2} \leq 24$ hours. Similarly, when the ranges of $\Sigma\sigma$ at 1 hour$\leq t_{1/2} \leq 1$ month and 1 hour$\leq t_{1/2} \leq 6$ months are calculated, $-0.19 \leq \Sigma\sigma \leq 0.41$ at the time of 1 hour$\leq t_{1/2} \leq 1$ month and $-0.19 \leq \Sigma\sigma \leq 0.57$ at the time of 1 hour$\leq t_{1/2} \leq 6$ months, respectively.

Further, in the case where formula (1) or formula (2) includes a 1,3-dioxone structure and at least one of $R^2$ and $R^5$ is a substituent other than a hydrogen atom, using the position constants (Es) of a phenyl group which has the largest influence of steric hindrance and a fluorine atom which has the smallest influence of steric hindrance among the substituents described above, the ranges of $\Sigma\sigma$ in a buffer at pH 5.5 and 37° C. at 1 hour$\leq t_{1/2} \leq 24$ hours, 1 hour$\leq t_{1/2} \leq 1$ month, and 1 hour$\leq t_{1/2} \leq 6$ months are calculated by using Taft's equation (11), respectively. As a result, it is found that $-0.98 \leq \Sigma\sigma \leq 0.00$ at the time of 1 hour$\leq t_{1/2} \leq 24$ hours, $-0.98 \leq \Sigma\sigma \leq 0.31$ at the time of 1 hour$\leq t_{1/2} \leq 1$ month, and $-0.98 \leq \Sigma\sigma \leq 0.48$ at the time of 1 hour$\leq t_{1/2} \leq 6$ months, respectively.

As described above, the kind and position of the substituent(s) suitable for imparting the desired hydrolyzability to the cyclic benzylidene acetal linker in the biodegradable polyethylene glycol derivative of the invention can be reasonably set by performing the calculation described above using equation (10) and equation (11).

$X^1$ in formula (1) or formula (2) of the invention is not particularly limited as long as it is a functional group which forms a covalent bond upon a reaction with a functional group present in a biofunctional molecule, for example, a physiologically active protein, a peptide, an antibody, a nucleic acid or a low molecular drug, or a drug carrier, for example, a liposome or a polymeric micelle, which is the object of chemical modification. For example, the functional groups include those described in "Harris, J. M. Poly(Ethylene Glycol) Chemistry; Plenum Press: New York, 1992", "Hermanson, G. T. Bioconjugate Techniques, 2nd ed.; Academic Press: San Diego, Calif., 2008", "PEGylated Protein Drugs: Basic Science and Clinical Applications; Veronese, F. M., Ed.; Birkhauser: Basel, Switzerland, 2009" and the like.

Preferred examples of $X^1$ include an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

More specifically, the functional group capable of forming a covalent bond upon a reaction with an amino group of the biofunctional molecule is an active ester group, an active carbonate group, an aldehyde group, an isocyanate group, an isothiocyanate group, an epoxy group, a maleimide group, a vinyl sulfone group, an acryl group, a sulfonyloxy group or a carboxy group, the functional group capable of forming a covalent bond upon a reaction with a thiol group of the biofunctional molecule is an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group or a vinyl group, the functional group capable of forming a covalent bond upon a reaction with an aldehyde group or a carboxy group of the biofunctional molecule is a thiol group, an amino group, an oxyamino group or a hydrazide group, the functional group capable of forming a covalent bond upon a reaction with an alkynyl group of the biofunctional molecules is a thiol group or an azide group, and the functional group capable of forming a covalent bond upon a reaction with an azide group of the biofunctional molecule is an alkynyl group.

The term "active ester" as referred to herein indicates an activated carboxy group represented by formula: —C(=O)-L, wherein L represents a leaving group.

The leaving group represented by L includes a succinimidyloxy group, a phthalimidyloxy group, a 4-nitrophenoxy group, a 1-imidazolyl group, a pentafluorophenoxy group, a benzotriazol-1-yloxy group, a 7-azabenzotriazol-1-yloxy group and the like. The term "active carbonate" as referred to herein indicates an activated carbonate group represented by formula: —O—C(=O)-L, wherein L represents a leaving group same as described above.

In a preferred embodiment of the invention, $X^1$ is a group represented by group (I), group (II), group (III), group (IV) or group (V).

Group (I): Functional group capable of forming a covalent bond upon a reaction with an amino group of the biofunctional molecule
(a), (b), (c), (d), (e) and (f) shown below:
Group (II): Functional group capable of forming a covalent bond upon a reaction with a thiol group of the biofunctional molecule
(a), (b), (c), (d), (e), (f), (g), (h), (i) and (j) shown below:
Group (III): Functional group capable of forming a covalent bond upon a reaction with an aldehyde group or a carboxy group of the biofunctional molecule
(g), (k), (l) and (m) shown below:
Group (IV): Functional group capable of forming a covalent bond upon a reaction with an alkynyl group of the biofunctional molecule
(g), (k), (l), (m) and (n) shown below:
Group (V): Functional group capable of forming a covalent bond upon a reaction with an azide group of the biofunctional molecule
(j) shown below:

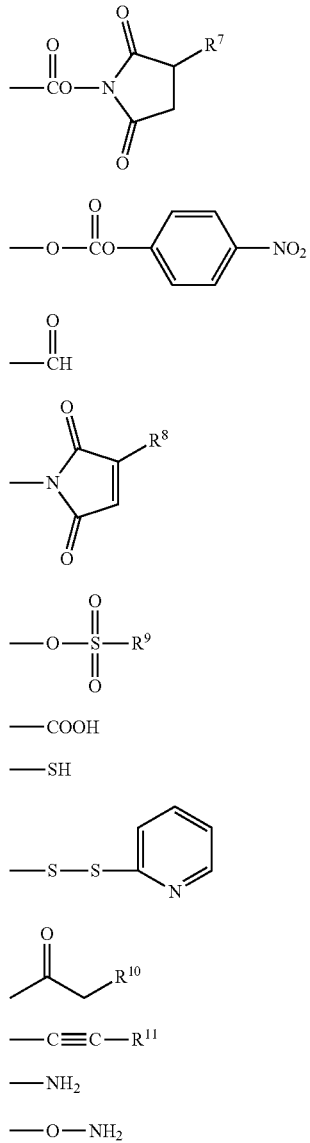

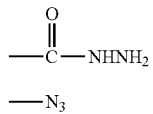

In the formulae above, $R^7$ is a hydrogen atom or a sulfo group, specific examples of the sulfo group include sodium sulfonate and potassium sulfonate, and $R^7$ is preferably a hydrogen atom. $R^8$ and $R^{11}$ are each a hydrogen atom or a hydrocarbon group having from 1 to 5 carbon atoms, and specific examples of the hydrocarbon group include a methyl group, an ethyl group, a propyl group, an isopropyl group, a butyl group, a tert-butyl group and a pentyl group. $R^9$ is a hydrocarbon group having from 1 to 10 carbon atoms which may contain a halogen atom, specific examples of the hydrocarbon group include a methyl group, an ethyl group, a propyl group, an isopropyl group, a butyl group, a tert-butyl group, a pentyl group, an isopentyl group, a hexyl group, a benzyl group, a 4-methylphenyl group, a trifluoromethyl group, a 2,2,2-trifluoroethyl group, a 4-(trifluoromethoxy)phenyl group, a vinyl group, a chloroethyl group, a bromoethyl group and an iodoethyl group, and $R^9$ is preferably a methyl group, a vinyl group, a 4-methylphenyl group or a 2,2,2-trifluoroethyl group. $R^{10}$ is a halogen atom selected from the group consisting of a chlorine atom, a bromine atom and an iodine atom.

$Z^1$ in formula (1) or formula (2) of the invention is a divalent spacer between the benzene ring of the cyclic benzylidene acetal group and the polyethylene glycol chain, $Z^2$ is a divalent spacer between the cyclic acetal of the cyclic benzylidene acetal group and the polyethylene glycol chain, and $Z^3$ is a divalent spacer between $X^1$ and the polyethylene glycol chain. These are composed of covalent bonds, are not particularly limited as long as they are more stable to acid hydrolysis than the cyclic benzylidene acetal group, and are preferably an ether bond, an ester bond, a carbonate bond, a urethane bond, an amide bond, a secondary amino group, an alkylene group containing any of these bonds and group, a single bond or an alkylene group. The number of carbon atoms of the alkylene group is preferably from 1 to 24. By way of illustration and without limitation, preferred examples of the alkylene group include structures such as (z1). Preferred examples of the alkylene group having an ether bond include structures such as (z2) or (z3). Preferred examples of the alkylene group having an ester bond include structures such as (z4). Preferred examples of the alkylene group having a carbonate bond include structures such as (z5). Preferred examples of the alkylene group having a urethane bond include structures such as (z6). Preferred examples of the alkylene group having an amide bond include structures such as (z7). Preferred examples of the alkylene group having a secondary amino group include structures such as (z8). In a preferred embodiment, p and q are each independently an integer of 1 to 12. However, in the case where at least one of $Z^1$, $Z^2$ and $Z^3$ is an ether bond, an ester bond, a carbonate bond, a urethane bond, an amide bond, a secondary amino group or an alkylene group containing any of these bonds and group and a plurality of identical structural units are connected, a number of the structural units described above is 2 or less.

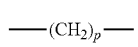 (z1)

-continued

 (z2)

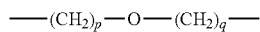 (z3)

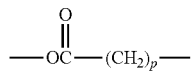 (z4)

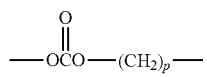 (z5)

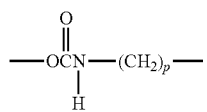 (z6)

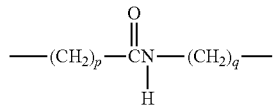 (z7)

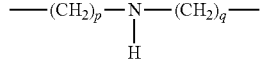 (z8)

$P^1$ in formula (1) or formula (2) of the invention is a straight-chain or branched polyethylene glycol having a number of ethylene glycol units of 3 or more, and $P^2$ is a straight-chain or branched polyethylene glycol having a number of ethylene glycol units of 3 or more. The number of the ethylene glycol units constituting $P^1$ or $P^2$ is more preferably 10 or more, and particularly preferably 20 or more. Further, the number of the ethylene glycol units constituting $P^1$ or $P^2$ is more preferably 2,000 or less, and particularly preferably 1,000 or less.

The term "polyethylene glycol" as used in the specification means both of polyethylene glycol having a molecular weight distribution obtained by polymerization of ethylene oxide and a monodispersed polyethylene glycol obtained by connecting of an oligoethylene glycol having a single molecular weight by a coupling reaction.

In one aspect of the invention, the biodegradable polyethylene glycol derivative in which w in formula (1) or formula (2) is 1 is provided.

In a preferred embodiment of the aspect, $P^1$ in formula (1) or formula (2) is a straight-chain polyethylene glycol having a hydrocarbon group or a chemically reactive functional group at the terminal thereof.

Specific examples of the straight-chain polyethylene glycol having a hydrocarbon group at the terminal thereof for $P^1$ include those represented by formula (3).

$$Y—(OCH_2CH_2)_n— \qquad (3)$$

In the formula, n is a number of repeating units per polyethylene glycol chain, and in the polyethylene glycol having a molecular weight distribution, it is defined that n is calculated by various theoretical calculations based on a number average molecular weight (Mn) of the compound.

In the formula, Y is a hydrocarbon group having from 1 to 24 carbon atoms, specific examples thereof include a methyl group, an ethyl group, a propyl group, an isopropyl group, a butyl group, a tert-butyl group, a pentyl group, an isopentyl group, a hexyl group, a heptyl group, a 2-ethylhexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a heneicosyl group, a docosyl group, a toicosyl group, a tetracosyl group, a phenyl group, a benzyl group, a cresyl group, a butylphenyl group, a dodecylphenyl group and a trityl group, and Y is preferably a hydrocarbon group having from 1 to 10 carbon atoms (more preferably from 1 to 7 carbon atoms), more preferably a methyl group or an ethyl group, and still more preferably a methyl group.

Specific examples of the straight-chain polyethylene glycol having a chemically reactive functional group for $P^1$ include those represented by formula (4).

$$X^2—Z^4—(OCH_2CH_2)_n— \qquad (4)$$

In the formula, $X^2$ is a chemically reactive functional group different from $X^1$, and $Z^4$ is a divalent spacer between the functional group $X^2$ and the polyethylene glycol chain. Since the biodegradable polyethylene glycol derivative has two different chemically reactive functional groups $X^1$ and $X^2$, it is possible to provide a polyethylene glycol-drug conjugate having a target-directing property, for example, by connecting a drug to $X^1$ and connecting a targeting molecule to $X^2$.

Preferred examples of $X^2$ include an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

More specifically, the functional group capable of forming a covalent bond upon a reaction with an amino group of the biofunctional molecule is an active ester group, an active carbonate group, an aldehyde group, an isocyanate group, an isothiocyanate group, an epoxy group, a maleimide group, a vinyl sulfone group, an acryl group, a sulfonyloxy group or a carboxy group, the functional group capable of forming a covalent bond upon a reaction with a thiol group of the biofunctional molecule is an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group or a vinyl group, the functional group capable of forming a covalent bond upon a reaction with an aldehyde group or a carboxy group of the biofunctional molecule is a thiol group, an amino group, an oxyamino group or a hydrazide group, the functional group capable of forming a covalent bond upon a reaction with an alkynyl group of the biofunctional molecule is a thiol group or an azide group, and the functional group capable of forming a covalent bond upon a reaction with an azide group of the biofunctional molecule is an alkynyl group.

In a preferred embodiment of the invention, $X^2$ is a group represented by group (I), group (II), group (III), group (IV) or group (V).

Group (I): Functional group capable of forming a covalent bond upon a reaction with an amino group of the biofunctional molecule
  (a), (b), (c), (d), (e) and (f) shown below:

Group (II): Functional group capable of forming a covalent bond upon a reaction with a thiol group of the biofunctional molecule (a), (b), (c), (d), (e), (f), (g), (h), (i) and (j) shown below:
Group (III): Functional group capable of forming a covalent bond upon a reaction with an aldehyde group or a carboxy group of the biofunctional molecule
(g), (k), (l) and (m) shown below:
Group (IV): Functional group capable of forming a covalent bond upon a reaction with an alkynyl group of the biofunctional molecule
(g), (k), (l), (m) and (n) shown below:
Group (V): Functional group capable of forming a covalent bond upon a reaction with an azide group of the biofunctional molecule
(j) shown below:

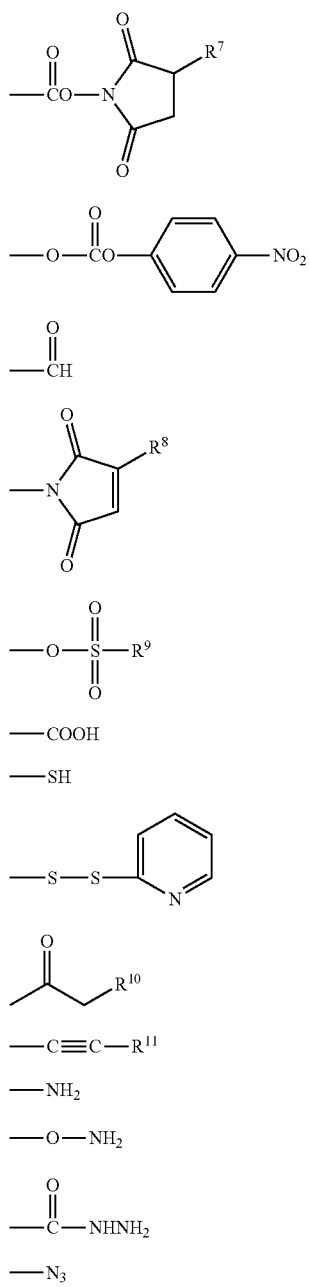

In the formulae above, $R^7$ is a hydrogen atom or a sulfo group, specific examples of the sulfo group include sodium sulfonate and potassium sulfonate, and $R^7$ is preferably a hydrogen atom. $R^8$ and $R^{11}$ are each a hydrogen atom or a hydrocarbon group having from 1 to 5 carbon atoms, and specific examples of the hydrocarbon group include a methyl group, an ethyl group, a propyl group, an isopropyl group, a butyl group, a tert-butyl group and a pentyl group. $R^9$ is a hydrocarbon group having from 1 to 10 carbon atoms which may contain a halogen atom, specific examples of the hydrocarbon group include a methyl group, an ethyl group, a propyl group, an isopropyl group, a butyl group, a tert-butyl group, a pentyl group, an isopentyl group, a hexyl group, a benzyl group, a 4-methylphenyl group, a trifluoromethyl group, a 2,2,2-trifluoroethyl group, a 4-(trifluoromethoxy)phenyl group, a vinyl group, a chloroethyl group, a bromoethyl group and an iodoethyl group, and $R^9$ is preferably a methyl group, a vinyl group, a 4-methylphenyl group or a 2,2,2-trifluoroethyl group. $R^{10}$ is a halogen atom selected from the group consisting of a chlorine atom, a bromine atom and an iodine atom.

It is necessary that $X^2$ is different from $X^1$. As to preferred examples of a combination of $X^1$ and $X^2$, when $X^1$ is an active ester group or an active carbonate group, $X^2$ is a group selected from a maleimide group, a vinyl sulfone group, an α-haloacetyl group, an alkynyl group and an azide group; when $X^1$ is an aldehyde group, $X^2$ is a group selected from a maleimide group, a vinyl sulfone group, an alkynyl group and an azide group; when $X^1$ is a maleimide group, a vinyl sulfone group or an α-haloacetyl group, $X^2$ is a group selected from an active ester group, an active carbonate group, an alkynyl group and an azide group; when $X^1$ is an alkynyl group or an azide group, $X^2$ is a group selected from a maleimide group, a vinyl sulfone group, an α-haloacetyl group, an active ester group, an active carbonate group, an amino group and an oxyamino group; when $X^1$ is an amino group or an oxyamino group, $X^2$ is an alkynyl group, an azide group, a thiol group or a carboxy group; and when $X^1$ is a thiol group, $X^2$ is a group selected from an amino group, an oxyamino group, an azide group and a carboxy group. More preferably, when $X^1$ is an active ester group or an active carbonate group, $X^2$ is a group selected from a maleimide group, an α-haloacetyl group, an alkynyl group and an azide group; when $X^1$ is an aldehyde group, $X^2$ is a group selected from a maleimide group, an α-haloacetyl group, an alkynyl group and an azide group; when $X^1$ is a maleimide group or an α-haloacetyl group, $X^2$ is a group selected from an active ester group, an active carbonate group, an alkynyl group and an azide group; when $X^1$ is an alkynyl group or an azide group, $X^2$ is a group selected from a maleimide group, an α-haloacetyl group, an active ester group, an active carbonate group, an amino group and an oxyamino group; when $X^1$ is an amino group or an oxyamino group, $X^2$ is an alkynyl group, an azide group or a thiol group; and when $X^1$ is a thiol group, $X^2$ is a group selected from an amino group, an oxyamino group and an azide group.

$Z^4$ is composed of covalent bonds, is not particularly limited as long as it is more stable to acid hydrolysis than the cyclic benzylidene acetal group, and is preferably an ether bond, an ester bond, a carbonate bond, a urethane bond, an amide bond, a secondary amino group, an alkylene group containing any of these bonds and group, a single bond or an alkylene group. The number of carbon atoms of the alkylene group is preferably from 1 to 24. By way of illustration and without limitation, preferred examples of the alkylene group include structures such as (z1) shown below. Preferred examples of the alkylene group having an ether bond include structures such as (z2) or (z3) shown below. Preferred examples of the alkylene group having an ester bond include structures such as (z4) shown below. Preferred examples of the alkylene group having a carbonate bond include structures such as (z5) shown below. Preferred examples of the alkylene group having a urethane bond include structures such as (z6) shown below. Preferred examples of the alkylene group having an amide bond include structures such as (z7) shown below. Preferred examples of the alkylene group having a secondary amino group include structures such as (z8) shown below. In a preferred embodiment, p and q are each independently an integer of 1 to 12. However, in the case where $Z^4$ is an ether bond, an ester bond, a carbonate bond, a urethane bond, an amide bond, a secondary amino group or an alkylene group containing any of these bonds and group and a plurality of identical structural units are connected, a number of the structural units described above is 2 or less.

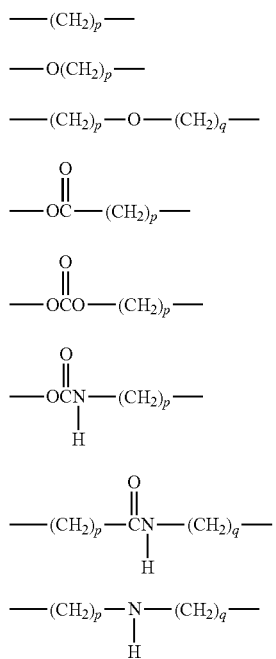

In another preferred embodiment of the aspect, $P^1$ in formula (1) or formula (2) is a branched polyethylene glycol having a hydrocarbon group or a chemically reactive functional group at the terminal thereof.

Specific examples of the branched polyethylene glycol having a hydrocarbon group at the terminal thereof for $P^1$ include those represented by formula (5).

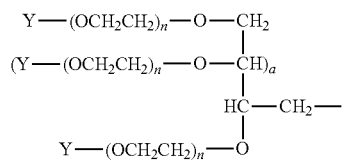

In the formula, Y is a hydrocarbon group having from 1 to 24 carbon atoms as described above, and a is 0 or 2.

In the case where a is 0, two polyethylene glycol chains are present and, in the case where a is 2, four polyethylene glycol chains are present. In general, in the chemical modification of a bio-related substance with polyethylene glycol, when connecting points to the polyethylene glycol are introduced more than necessary, the active sites of the bio-related substance are destroyed to reduce its function so that an attempt to increase the effect by increasing a molecular weight of the polyethylene glycol has been performed. However, the viscosity increases with the increase in the molecular weight and hence, for example, handling as an aqueous solution preparation, for example, an injection preparation becomes difficult. Since the polyethylene glycol derivative has a branched structure, it shows low viscosity in comparison with a straight-chain polyethylene glycol derivative having the same molecular weight, and thus it is useful in application, for example, the aqueous solution preparation.

Specific examples of the branched polyethylene glycol having a chemically reactive functional group at the terminal thereof for $P^1$ include those represented by formula (6).

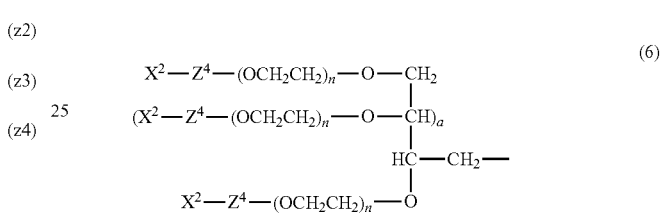

In the formula, $X^2$ is a chemically reactive functional group different from $X^1$ as described above, $Z^4$ is a divalent spacer as described above, and a is 0 or 2.

The polyethylene glycol derivative in which $P^1$ is represented by formula (6) has one $X^1$ and two or four $X^2$ in the case where v in formula (1) or formula (2) is 1 and, for example, when a drug is connected to $X^1$ and a targeting molecule is connected to $X^2$, high target-directing performance can be obtained.

In another aspect of the invention, the biodegradable polyethylene glycol derivative in which w in formula (1) or formula (2) is from 2 to 8 is provided.

In a preferred embodiment of the aspect, $P^1$ in formula (1) or formula (2) is represented by formula (7).

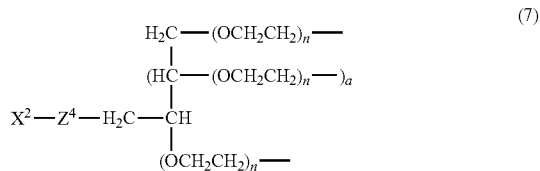

In the formula, $X^2$ is a chemically reactive functional group different from $X^1$ as described above, $Z^4$ is a divalent spacer as described above, and a is 0 or 2.

In the antibody-drug conjugate (ADC)-related field, in order to increase drug transportation efficiency, it is preferred to connect a plurality of drugs to an antibody, but when a plurality of connecting points are introduced into the antibody, a problem arises in that the affinity to an antigen is decreased. The polyethylene glycol derivative in which $P^1$ is represented by formula (7) has two or four $X^1$ and one $X^2$ in the case where v in formula (1) or formula (2) is 1 and, for example, when an anticancer agent is connected to $X^1$ and an antibody is connected to $X^2$ in ADC targeting cancer, it is possible to improve the transportation efficiency of the anticancer agent without increasing the connecting points to the antibody.

In another preferred embodiment of the aspect, $P^1$ in formula (1) or formula (2) is polyethylene glycol having the number of terminals of 2 to 8, all the terminals of the polyethylene glycol constituting $P^1$ are each connected to $Z^1$ in formula (1) or $Z^2$ in formula (2), and w is equal to the number of terminals of the polyethylene glycol.

In specific examples of the embodiment, $P^1$ in formula (1) or formula (2) is selected from the group consisting of formula (r), formula (s), formula (t), formula (u) and formula (v). w is 2 in the case where $P^1$ is represented by formula (r), w is 3 in the case where $P^1$ is represented by formula (s), w is 4 in the case where $P^1$ is represented by formula (t), w is 4 in the case where $P^1$ is represented by formula (u), and w is 8 in the case where $P^1$ is represented by formula (v).

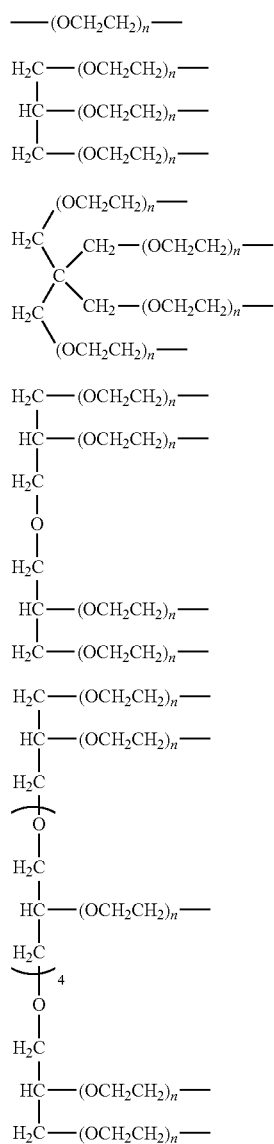

A preferred range of n in formula (3), formula (4) or formula (r) of the invention is an integer of 3 to 2,000, more preferably an integer of 20 to 1,000, and still more prefer-ably an integer of 40 to 500. Further, a preferred range of n in formula (5), formula (6), formula (7), formula (s), formula (t), formula (u) and formula (v) is preferably an integer of 3 to 1,000, more preferably an integer of 10 to 500, and still more preferably an integer of 20 to 250.

In one aspect of the invention, $P^2$ in formula (1) or formula (2) is represented by formula (8). Here, v in formula (1) or formula (2) is 1.

In the formula, m is a number of repeating units per polyethylene glycol chain, and in a polyethylene glycol having a molecular weight distribution, it is defined that m is calculated by various theoretical calculations based on a number average molecular weight (Mn) of the compound.

In another aspect of the invention, $P^2$ in formula (1) or formula (2) is represented by formula (9).

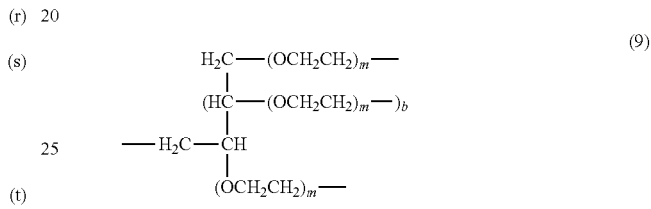

In the formula, b is 0 or 2. Here, v in formula (1) or formula (2) is b+2.

A preferred range of m in formula (8) of the invention is an integer of 3 to 2,000, more preferably an integer of 20 to 1,000, and still more preferably an integer of 40 to 500. Further, a preferred range of m in formula (9) is preferably an integer of 3 to 1,000, more preferably an integer of 10 to 500, and still more preferably an integer of 20 to 250.

The biodegradable polyethylene glycol derivative of the invention can be synthesized by linking a polyethylene glycol intermediate composed of $P^2$ to a polyethylene glycol intermediate composed of $P^1$ through a cyclic benzylidene acetal linker having substituent(s). The bond generated by the linking is determined by a combination of the functional groups used in the reaction, and is the ether bond, the ester bond, the carbonate bond, the urethane bond, the amide bond, the secondary amino group, the alkylene group containing any of these bonds and group, the single bond or the alkylene group contained in the divalent spacer $Z^1$ and $Z^2$ described above. In the biodegradable polyethylene glycol derivative synthesized, the terminal functional group is chemically converted, if desired. As to the reaction used for the functional group conversion, a conventionally known method can be used, but it is necessary to appropriately select conditions which do not decompose the cyclic benzylidene acetal group of formula (1) or formula (2) and the bonds contained in the divalent spacers $Z^1$, $Z^2$, $Z^3$ and $Z^4$ described above. In addition, in the synthesis of the biodegradable polyethylene glycol derivative, the cyclic benzylidene acetal linker compound for introducing the cyclic benzylidene acetal linker either may be connected to the polyethylene glycol intermediate composed of $P^1$ and then connected to the polyethylene glycol intermediate composed of $P^2$ or may be connected to the polyethylene glycol intermediate composed of $P^2$ and then connected to the polyethylene glycol intermediate composed of $P^1$. As a typical example of the synthesis of the biodegradable polyethylene glycol derivative, the steps described below are exemplified. A synthesis method of the biodegradable polyethylene glycol derivative represented by formula (1) is described herein as the typical example.

(A) Cyclic Benzylidene Acetal Linker Compound

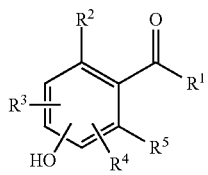
(17)

in the formula, $R^1$ is a hydrogen atom or a hydrocarbon group; and $R^2$, $R^3$, $R^4$ and $R^5$ are each independently an electron-withdrawing or electron-donating substituent or a hydrogen atom.

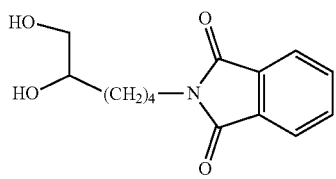
(18)

A carbonyl compound of formula (17) having a hydroxy group which is a chemically reactive functional group is allowed to react with a 1,2-diol derivative of formula (18) having a phthalimide group in which an amino group is protected with a phthaloyl group in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an acid catalyst to obtain a compound of formula (19) shown below having a cyclic benzylidene acetal group. The resulting compound may be purified by extraction, recrystallization, adsorbent treatment, column chromatography or the like. In place of the carbonyl compound, it is possible to use a corresponding acetal derivative of a lower alcohol. The lower alcohol is preferably an alcohol having from 1 to 5 carbon atoms, and more preferably methanol or ethanol. The acid catalyst may be either an organic acid or an inorganic acid and is not particularly limited, and specific examples thereof include p-toluenesulfonic acid, pyridinium p-toluenesulfonate, methanesulfonic acid, 10-camphorsulfonic acid, hydrogen chloride, iodine, ammonium chloride, oxalic acid, boron trifluoride-diethyl ether complex and the like.

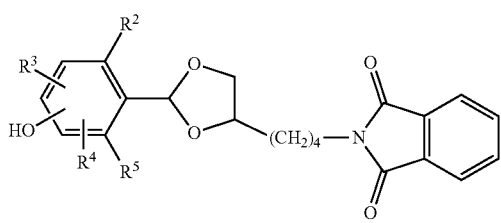
(19)

The "protective group" as referred to herein is a component which prevents or blocks a reaction of a specific chemically reactive functional group in the molecule under certain reaction conditions. The protective group varies depending on the kind of the chemically reactive functional group to be protected, the conditions to be used and the presence of the other functional group or protective group in the molecule. Specific examples of the protective group can be found in many general books and are described, for example, in "Wuts, P. G. M.; Greene, T. W., Protective Groups in Organic Synthesis, 4th ed.; Wiley-Interscience: New York, 2007". Moreover, the functional group protected by the protective group can be reproduce the original functional group by deprotection using reaction conditions suitable for each of the protective groups, that is, causing a chemical reaction. Therefore, in the specification, a functional group which is protected by a protective group and is capable of being deprotected by various reactions is included in the "chemically reactive functional group". The typical deprotection conditions of the protective group are described in the literature described above.

As the chemically reactive functional group in the compound of formula (17), a functional group other than the hydroxy group can also be used. Specific examples thereof include a hydroxyalkyl group, an amino group, an aminoalkyl group, a carboxy group and a carboxyalkyl group. Also, the functional group described above may be protected by a protective group which is stable in the acidic conditions of the acetalization reaction and can be deprotected under reaction conditions other than catalytic reduction by which the cyclic benzylidene acetal group is decomposed. As to preferred combinations of the functional group to be protected and the protective group, when the functional group to be protected is a hydroxy group or a hydroxyalkyl group, for example, a silyl protective group and an acyl protective group are exemplified, and specific examples thereof include a tert-butyldiphenylsilyl group, a tert-butyldimethylsilyl group, a triisopropylsilyl group, an acetyl group and a pivaloyl group. When the functional group to be protected is an amino group or an aminoalkyl group, for example, an acyl protective group and a carbamate protective group are exemplified, and specific examples thereof include a trifluoroacetyl group, a 9-fluorenylmethyloxycarbonyl group and a 2-(trimethylsilyl)ethyloxycarbonyl group. When the functional group to be protected is a carboxy group or a carboxyalkyl group, for example, an alkyl ester protective group and a silyl ester protective group are exemplified, and specific examples thereof include a methyl group, a 9-fluorenylmethyl group and a tert-butyldimethylsilyl group. The kinds and the typical deprotection conditions of the specific protective groups are described in the literature described above, and the reaction conditions suitable for each of the protective groups are selected and the deprotection can be performed before the reaction with the hydrophilic polymer intermediate.

Moreover, as the chemically reactive functional group excepting the 1,2-diol moiety in the compound of formula (18), a functional group other than the phthalimide group can also be used. In the case where the chemically reactive functional group is a functional group which is protected by a protective group, it is necessary that the protective group is stable in the acidic conditions of the acetalization reaction and can be deprotected under reaction conditions other than catalytic reduction by which the benzylidene acetal group is decomposed.

As to preferred combinations of the functional group to be protected and the protective group, when the functional group to be protected is an amino group, for example, an acyl protective group and a carbamate protective group are exemplified, and specific examples thereof include a trifluoroacetyl group, a 9-fluorenylmethyloxycarbonyl group and a 2-(trimethylsilyl)ethyloxycarbonyl group. When the functional group to be protected is a hydroxy group, for example, a silyl protective group and an acyl protective group are exemplified, and specific examples thereof include a tert-butyldiphenylsilyl group, a tert-butyldimethylsilyl group, a triisopropylsilyl group, an acetyl group and a pivaloyl group. When the functional group to be protected is a carboxy group, for example, an alkyl ester protective group and a silyl ester protective group are exemplified, and specific examples thereof include a methyl group, a 9-fluorenylmethyl group and a tert-butyldimethylsilyl group. When the functional group to be protected is a sulfanyl group, for example, a thioether protective group, a thiocarbonate protective group and a disulfide protective group are exemplified, and specific examples thereof include an S-2,4-dinotrophenyl group, an S-9-fluorenylmethyloxycarbonyl group and an S-tert-butyldisulfide group. The typical deprotection conditions of the protective group are described in the literature described above, and the reaction conditions suitable for each of the protective groups are selected. However, in the case where the chemically reactive functional group is a functional group which does not inhibit the acetalization reaction even when it is not protected by a protective group, it is not necessary to use a protective group.

(B) Polyethylene Glycol Intermediate Composed of $P^1$

Ethylene oxide is polymerized in an amount of 3 to 2,000 molar equivalents to methanol, which is an initiator, in toluene or with no solvent under alkaline conditions, for example, metallic sodium, metallic potassium, sodium hydride or potassium hydride to obtain polyethylene glycol of formula (20). The initiator is preferably an alcohol having a hydrocarbon group having from 1 to 24 carbon atoms, and specifically includes, for example, methanol, ethanol, propanol, isopropanol, butanol, tert-butanol, phenol and benzyl alcohol. Since the polyethylene glycol has a hydroxy group which is a chemically reactive functional group, it can be used as it is in a reaction with a cyclic benzylidene acetal linker compound.

$$CH_3—(OCH_2CH_2)_n—OH \qquad (20)$$

The polyethylene glycol of formula (20) is allowed to react with methanesulfonyl chloride in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, pyridine or 4-dimethylaminopyridine or an inorganic base, for example, sodium carbonate, sodium hydrogen carbonate, sodium acetate or potassium carbonate to obtain a polyethylene glycol intermediate of formula (21). The organic base and inorganic base may not be used. The use ratio of the organic base or the inorganic base is not particularly limited, and is preferably equimolar or more to the hydroxy group of the polyethylene glycol of formula (20). Also, it is possible to use the organic base as a solvent. The resulting compound may be purified by a purification means, for example, extraction, recrystallization, adsorbent treatment, reprecipitation, column chromatography or supercritical extraction.

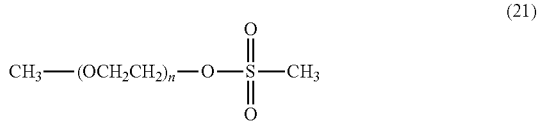

As the chemically reactive functional group in the polyethylene glycol intermediate of formula (21), other functional groups can be also used. Preferred examples of the chemically reactive functional group are functional groups wherein the bond generated by the reaction of the polyethylene glycol intermediate with the cyclic benzylidene acetal linker compound described above becomes the ether bond, the ester bond, the carbonate bond, the urethane bond, the amide bond, the secondary amino group, the alkylene group containing any of these bonds and group, the single bond or the alkylene group contained in the divalent spacer $Z^1$ of formula (1), and specifically include, for example, a halogen atom, an active ester, an active carbonate, an aldehyde group, an amino group, a hydroxy group and a carboxy group.

(C) Reaction Between Cyclic Benzylidene Acetal Linker Compound and Polyethylene Glycol Intermediate Composed of $P^1$ The benzylidene acetal linker compound of formula (19) and the polyethylene glycol intermediate of formula (21) are subjected to a reaction in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, potassium tert-butoxide or sodium hexamethyldisilazane or an inorganic base, for example, potassium carbonate, potassium hydroxide or sodium hydride to obtain a compound of formula (22). The use ratio of the organic base or the inorganic base is not particularly limited, and is preferably equimolar or more to the chemically reactive functional group of the polyethylene glycol intermediate of formula (21). Also, it is possible to use the organic base as a solvent. The resulting compound may be purified by the purification means described above.

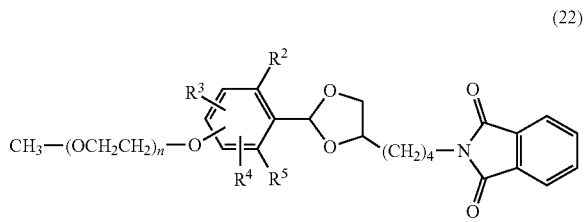

The chemically reactive functional group of the cyclic benzylidene acetal linker compound may be subjected to functional group conversion before the reaction with the polyethylene glycol intermediate. The reaction conditions for the reaction between the cyclic benzylidene acetal linker compound and the polyethylene glycol intermediate are determined depending on the combination of the chemically reactive functional group of the cyclic benzylidene acetal linker compound and the chemically reactive functional group of the polyethylene glycol intermediate and a conventionally known method can be used. However, it is necessary to appropriately select conditions which do not decompose the bonds contained in the cyclic benzylidene acetal group and the divalent spacers $Z^1$ and $Z^2$ described above of formula (1) or formula (2).

The compound of formula (22) is treated by using a basic organic compound, for example, ethylenediamine, methyl hydrazine or methylamine or a basic inorganic compound, for example, hydrazine, hydroxylamine or sodium hydroxide in a protic solvent, for example, water, methanol or ethanol, in an aprotic solvent, for example, acetonitrile, tetrahydrofuran, dimethyl sulfoxide, dimethylformamide or dimethylacetamide or with no solvent to obtain a compound of formula (23) in which the phthalimide group is deprotected and converted into an amino group. The use ratio of the basic compound is not particularly limited, and is preferably equimolar or more to the chemically reactive functional group of the compound of formula (22). Also, it is possible to use the basic compound as a solvent. The resulting compound may be purified by the purification means described above.

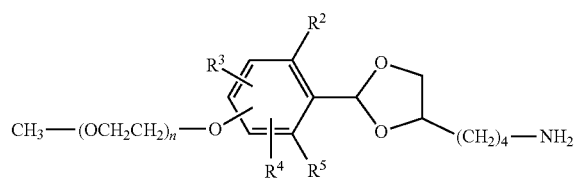
(23)

(D) Polyethylene Glycol Intermediate Composed of $P^2$

The polyethylene glycol intermediate composed of $P^2$ has chemically reactive functional groups at at least two terminals of polyethylene glycol, and preferred examples of the chemically reactive functional group include an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group, an azide group and a hydroxy group. More specifically, the functional group capable of forming a covalent bond upon a reaction with an amino group of the cyclic acetal linker is an active ester group, an active carbonate group, an aldehyde group, an isocyanate group, an isothiocyanate group, an epoxy group, a maleimide group, a vinyl sulfone group, an acryl group, a sulfonyloxy group or a carboxy group, the functional group capable of forming a covalent bond upon a reaction with a thiol group of the cyclic acetal linker is an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group or a vinyl group, the functional group capable of forming a covalent bond upon a reaction with an aldehyde group or a carboxy group of the cyclic acetal linker is a thiol group, an amino group, an oxyamino group, a hydrazide group or a hydroxy group, the functional group capable of forming a covalent bond upon a reaction with an alkynyl group of the cyclic acetal linker is a thiol group or an azide group, and the functional group capable of forming a covalent bond upon a reaction with an azide group of the cyclic acetal linker is an alkynyl group.

The chemically reactive functional groups in the polyethylene glycol intermediate composed of $P^2$ may be the same or different, and a combination of two different functional groups is preferred.

As to preferred examples of the combination of two different functional groups, when one is an active ester group or an active carbonate group, the other is a group selected from a maleimide group, a vinyl sulfone group, an α-haloacetyl group, an alkynyl group and an azide group, when one is an aldehyde group, the other is a group selected from a maleimide group, a vinyl sulfone group, an alkynyl group and an azide group, when one is a maleimide group, a vinyl sulfone group or an α-haloacetyl group, the other is a group selected from an active ester group, an active carbonate group, an alkynyl group and an azide group, when one is an alkynyl group or an azide group, the other is a group selected from a maleimide group, a vinyl sulfone group, an α-haloacetyl group, an active ester group, an active carbonate group, an amino group, an oxyamino group and a hydroxy group, when one is an amino group or an oxyamino group, the other is an alkynyl group, an azide group, a thiol group, a hydroxy group or a carboxy group, and when one is a thiol group or a hydroxy group, the other is a group selected from an amino group, an oxyamino group, an azide group and a carboxy group. More preferably, when one is an active ester group or an active carbonate group, the other is a group selected from a maleimide group, an α-haloacetyl group, an alkynyl group and an azide group, when one is an aldehyde group, the other is a group selected from a maleimide group, an α-haloacetyl group, an alkynyl group and an azide group, when one is a maleimide group or an α-haloacetyl group, the other is a group selected from an active ester group, an active carbonate group, an alkynyl group and an azide group, when one is an alkynyl group or an azide group, the other is a group selected from a maleimide group, an α-haloacetyl group, an active ester group, an active carbonate group, an amino group, an oxyamino group or a hydroxy group, when one is an amino group or an oxyamino group, the other is an alkynyl group, an azide group, a hydroxy group or a thiol group, and when one is a thiol group or a hydroxy group, the other is a group selected from an amino group, an oxyamino group and an azide group.

Further, of the chemically reactive functional groups in the polyethylene glycol intermediate composed of $P^2$, the functional group other than the functional groups reacted with the cyclic acetal linker may be protected with a protective group which is stable under the reaction conditions of the reaction with the cyclic acetal linker and can be deprotected under reaction conditions other than catalytic reduction by which the cyclic benzylidene acetal group is decomposed. As to preferred combinations of the functional group to be protected and the protective group, when the functional group to be protected is an amino group, for example, an acyl protective group and a carbamate protective group are exemplified, and specific examples thereof include a trifluoroacetyl group, a phthalimide group, a 9-fluorenylmethyloxycarbonyl group and a 2-(trimethylsilyl)ethyloxycarbonyl group. When the functional group to be protected is a hydroxy group, for example, a silyl protective group and an acyl protective group are exemplified, and specific examples thereof include a tert-butyldiphenylsilyl group, a tert-butyldimethylsilyl group, a triisopropylsilyl group, an acetyl group and a pivaloyl group. When the functional group to be protected is a carboxy group, for example, an alkyl ester protective group and a silyl ester protective group are exemplified, and specific examples thereof include a methyl group, a 9-fluorenylmethyl group and a tert-butyldimethylsilyl group. When the

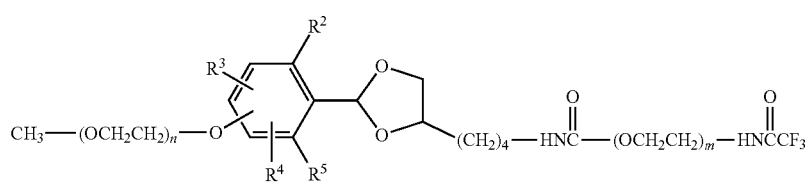

(25)

functional group to be protected is a sulfanyl group, for example, a thioether protective group, a thiocarbonate protective group and a disulfide protective group are exemplified, and specific examples thereof include an S-2,4-dinotrophenyl group, an S-9-fluorenylmethyloxycarbonyl group and an S-tert-butyldisulfide group. The typical deprotection conditions of the protective group are described in the literature described above, and the reaction conditions suitable for each of the protective groups are selected. However, in the case where the chemically reactive functional group is a functional group which does not inhibit the reaction with the cyclic acetal linker even when it is not protected by a protective group, it is not necessary to use a protective group.

The description will be made here using the compound of formula (24) having an amino group protected with a trifluoroacetyl group at one terminal of a straight-chain polyethylene glycol and an N-succinimidylcarbonate, which is an active carbonate group, at the other terminal thereof. Preferred examples of the polyethylene glycol having the combination of two different functional groups are described, for example, in NOF Corporation (Tokyo, Japan; see www.nof.co.jp/english: Catalogue Ver. 15), but it is not limited thereto.

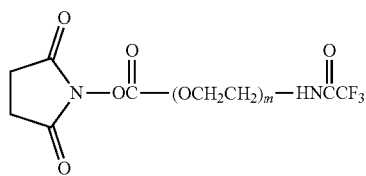

(24)

(E) Reaction Between Polyethylene Glycol Intermediate Composed of $P^1$ Having Cyclic Benzylidene Acetal Linker and Polyethylene Glycol Intermediate Composed of $P^2$ The compound of formula (23) is allowed to react with the compound of formula (24) in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, pyridine or 4-dimethylaminopyridine or an inorganic base, for example, sodium carbonate, sodium hydrogen carbonate, sodium acetate or potassium carbonate to obtain a compound of formula (25), which is a biodegradable polyethylene glycol derivative having a cyclic benzylidene acetal linker. The organic base or the inorganic base may not be used. The use ratio of the organic base or the inorganic base is not particularly limited, and is preferably equimolar or more to the chemically reactive functional group of the compound of formula (23). Also, it is possible to use the organic base as a solvent.

The reaction conditions of the reaction between the polyethylene glycol intermediate composed of $P^1$ and the polyethylene glycol intermediate composed of $P^2$ are determined depending on the combination of the chemically reactive functional group of the polyethylene glycol intermediate composed of $P^1$ and the chemically reactive functional group of the polyethylene glycol intermediate composed of $P^2$ and a conventionally known method can be used. However, it is necessary to appropriately select conditions which do not decompose the bonds contained in the cyclic benzylidene acetal group and the divalent spacers $Z^1$, $Z^2$ and $Z^3$ described above of formula (1) or formula (2).

The resulting compound may be purified by a purification means, for example, extraction, recrystallization, adsorbent treatment, reprecipitation, column chromatography or supercritical extraction.

As the adsorbent in the case of performing purification by the adsorbent treatment, an inorganic adsorbent composed of an oxide containing at least one of aluminum and silicon. Specifically, it includes an oxide containing either one of aluminum and silicon or both of them. More specifically, it includes aluminum oxide, silicon dioxide, a complex oxide of aluminum oxide and silicon dioxide, a complex oxide of aluminum oxide and other metal, and a complex oxide of silicon dioxide and other metal. The other metal includes sodium, magnesium and potassium.

In the adsorption purification described above, in order to remove impurities having an acidic functional group, an adsorbent having an acidic substance adsorption ability is preferred, and specific examples thereof include Kyoward 300 ($2.5MgO.Al_2O_3.O.7CO_3.nH_2O$), Kyoward 500 ($Mg_6Al_2(OH)_{16}(CO_3)_4H_2O$) and Kyoward 1000 ($Mg_{4.5}Al_2(OH)_{13}(CO_3).3.5H_2O$) of Kyoward series of Kyowa Chemical Industry Co., Ltd. The adsorbents may be used individually or in combination.

Further, in the adsorption purification described above, in order to remove impurities having a basic functional group, an adsorbent having a basic substance adsorption ability is preferred, and specific examples thereof include an adsorbent having a basic substance adsorption ability, for example, Kyoward 600 ($MgO.3SiO_2.nH_2O$), Kyoward 700 ($Al_2O_3.9SiO_2.nH_2O$) or Kyoward 200B ($Al_2O_3.9SiO_2.nH_2O$), preferably Kyoward 700 ($Al_2O_3.9SiO_2.nH_2O$) or Kyoward 200B ($Al_2O_3.9SiO_2.nH_2O$). The adsorbents may be used individually or in combination with other adsorbents.

Furthermore, in the adsorption purification described above, in order to remove a neutralized salt, an adsorbent having a high salt adsorption ability is preferred, and specific examples thereof include Kyoward 2000 ($4.5MgO.Al_2O_3$)

and Kyoward 200B ($Al_2O_3 \cdot 9SiO_2 \cdot nH_2O$). The adsorbents may be used individually or in combination.

(F) Terminal Functional Group Conversion of Biodegradable Polyethylene Glycol Derivative Having Cyclic Benzylidene Acetal Linker The compound of formula (25) is treated by using a basic organic compound, for example, ethylenediamine, methyl hydrazine or methylamine or a basic inorganic compound, for example, hydrazine, hydroxylamine, potassium carbonate or sodium hydroxide in a protic solvent, for example, water, methanol or ethanol, in an aprotic solvent, for example, acetonitrile, tetrahydrofuran, dimethyl sulfoxide, dimethylformamide or dimethylacetamide or with no solvent to obtain a compound of formula (26) in which the trifluoroacetyl group is deprotected and converted into an amino group. The use ratio of the basic compound is not particularly limited, and is preferably equimolar or more to the chemically reactive functional group of the compound of formula (25). Also, it is possible to use the basic compound as a solvent. The resulting compound may be purified by the purification means described above.

can be used, but it is necessary to appropriately select conditions which do not decompose the bonds contained in the cyclic benzylidene acetal group and the divalent spacers $Z^1$, $Z^2$ and $Z^3$ described above of formula (1) or formula (2).

In formula (1) and formula (2), although the direction of connection of the cyclic benzylidene acetal linker with respect to $P^1$ and $P^2$ is opposite, the cyclic benzylidene acetal linker compound for introducing the cyclic benzylidene acetal linker either may be connected to the polyethylene glycol intermediate composed of $P^1$ and then connected to the polyethylene glycol intermediate composed of $P^2$ or may be connected to the polyethylene glycol intermediate composed of $P^2$ and then connected to the polyethylene glycol intermediate composed of $P^1$, and the compound represented by formula (1) and the compound represented by formula (2) can be synthesized according to essentially the same technique. In addition, synthesis examples of the compounds represented by formula (1) and formula (2) are specifically shown in the example below, and it will be understood by those skilled in the art that these compounds can be synthesized according to essentially the same technique.

(26)

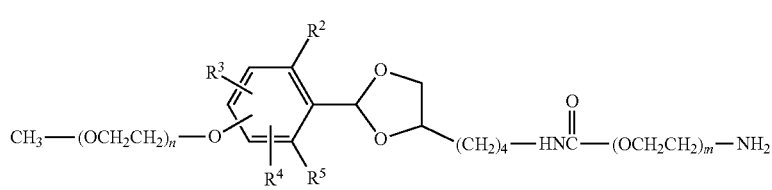

Further, the compound of formula (26) is allowed to react with N-succinimidyl 3-maleimidopropionate in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, pyridine or 4-dimethylaminopyridine or an inorganic base, for example, sodium carbonate, sodium hydrogen carbonate, sodium acetate or potassium carbonate to obtain a compound of formula (27) in which a maleimide group is introduced into the terminal. The organic base and inorganic base may not be used. The use ratio of the organic base or the inorganic base is not particularly limited, and is preferably equimolar or more to the chemically reactive functional group of the compound of formula (26). Also, it is possible to use the organic base as a solvent. The resulting compound may be purified by the purification means described above.

EXAMPLES

The invention will be described more specifically with reference to the examples, but the invention should not be construed as being limited thereto.

In $^1$H-NMR analysis, JNM-ECP400 or JNM-ECA600 produced by JEOL DATUM Ltd. was used. For the measurement, a tube of 5 mm was used, and tetramethylsilane (TMS) was used as an internal standard substance in the case where a deuterated solvent was $CDCl_3$, $CD_3CN$ or $CD_3OD$, or HDO was used as a standard in the case of $D_2O$.

In gel permeation chromatography (GPC) analysis, there were used SHODEX GPC SYSTEM-11 as a GPC system, SHODEX RIX8 as a differential refractometer which was a detector, and three columns, i.e., SHODEX KF801L, KF803L and KF804L (φ8 mm×300 mm) connected in series as GPC columns, and the temperature of the column oven was set to 40° C. The measurement was performed using tetrahydrofuran as an eluent, at the flow rate of 1 mL/min, (27)

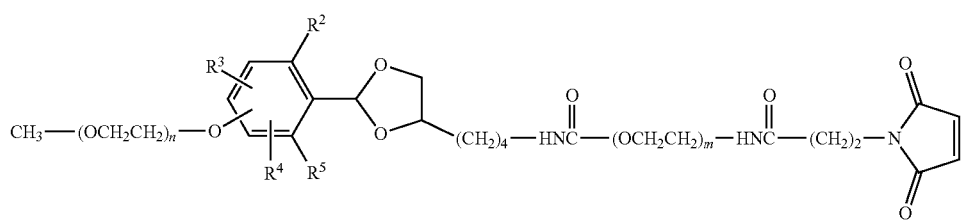

For the terminal functional group conversion of a biodegradable polyethylene glycol derivative having a cyclic benzylidene acetal linker, a conventionally known method at the sample concentration of 0.1% by weight, and in the injection volume of 0.1 mL. The calibration curves prepared by using ethylene glycol, diethylene glycol and triethylene glycol produced by Kanto Chemical Co., Ltd. and Polymer Standards for GPC of polyethylene glycol or polyethylene oxide having a molecular weight of 600 to 70,000 produced by Polymer Laboratory Co., Ltd were used. For analysis of data, BORWIN GPC calculation program was used. Mn represents a number average molecular weight, Mw represents a weight average molecular weight, and a molecular weight distribution is indicated as a calculated value of Mw/Mn.

A deuterated water buffer of MES (2-morpholinoethanesulfonic acid) having pD of 5.5 and a deuterated water buffer of HEPES (2-[4-(Hydroxyethyl)-1-piperazinyl]ethanesulfonic acid) having pD of 7.4 for use in hydrolysis test were prepared by adding a 0.1M sodium hydroxide deuterated water solution to a 0.1M MES deuterated water solution and a 0.1M HEPES deuterated water solution, respectively, based on the relational equation shown below described in "Glasoe, P. K.; Long, F. A., J. Phys. Chem. 1960, 64, 188-190".

pD=Measured value by pH meter+0.40

The hydrolysis ratio of each of the compounds of formula (35), formula (44), formula (45), formula (47) and formula (48) was evaluated by $^1$H-NMR and calculated according to the calculation equation shown below by taking an integrated value of the hydrogen of the acetal group and an integral value of the hydrogen of the aldehyde group to be formed by hydrolysis as $I^1$ and $I^2$, respectively.

Hydrolysis ratio (%)=[$I^2$/($I^1$+$I^2$)]×100

The hydrolysis ratio of each of the compounds of formula (41) and formula (54) was evaluated by GPC and calculated according to the calculation equation shown below by taking a peak area of polyethylene glycol (molecular weight: about 10,000) which was not divided upon the hydrolysis of the linker and a peak area of polyethylene glycol (molecular weight: about 5,000) which was divided upon the hydrolysis of the linker as $A^1$ and $A^2$, respectively.

Hydrolysis ratio (%)=[$A^2$/($A^1$+$A^2$)]×100

The hydrolysis ratio of each of the compounds of formula (74) and formula (76) was evaluated by GPC and calculated according to the calculation equation shown below by taking a peak area of polyethylene glycol (molecular weight: about 15,000) which was not divided upon the hydrolysis of the linker, a peak area of polyethylene glycol (molecular weight: about 10,000) which is partially divided upon the hydrolysis of the linker and a peak area of polyethylene glycol (molecular weight: about 5,000) which was completely divided upon the hydrolysis of the linker as $A^1$, $A^2$ and $A^3$, respectively.

Hydrolysis ratio (%)=[$A^3$/($A^1$+$A^2$+$A^3$)]×100

Example 1

Into a 200 mL three-necked flask equipped with a thermometer, a nitrogen inlet tube, a stirrer, a Dean-stark tube and a condenser tube were charged 1,2,6-hexanetriol (30.0 g, 0.224 mol), acetone dimethyl acetal (25.6 g, 0.246 mol) and p-toluenesulfonic acid monohydrate (0.426 g, 2.24 mmol), and the reaction was performed at 80° C. for 3 hours while distilling off methanol. Triethylamine (0.453 g, 4.48 mmol) was added thereto and the mixture was stirred for a while, diluted with ethyl acetate, and washed with an aqueous 20% by weight sodium chloride solution. The organic layer was dried over anhydrous sodium sulfate, and after filtration, the solvent was distilled off under a reduced pressure. The residue was purified by silica gel chromatography to obtain a compound of formula (28).

$^1$H-NMR (CDCl$_3$, internal standard TMS); δ (ppm):
1.35 (3H, s, —C$\underline{H}_3$), 1.41 (3H, s, —C$\underline{H}_3$), 1.49-1.67 (6H, m, >CHC$\underline{H}_2$C$\underline{H}_2$C$\underline{H}_2$—), 2.07 (1H, brs, —O$\underline{H}$), 3.51 (1H, t, —OC$\underline{H}_2$CH<), 3.64 (2H, t, —C$\underline{H}_2$OH), 4.04 (1H, dd, —OCH$_2$CH<), 4.07-4.10 (1H, m, —OCH$_2$C$\underline{H}$<)

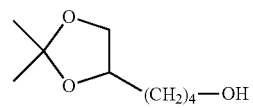

(28)

Example 2

Into a 500 mL four-necked flask equipped with a thermometer, a nitrogen inlet tube, a stirrer and a condenser tube were charged the compound of formula (28) (20.0 g, 0.115 mol), triethylamine (23.3 g, 0.230 mol) and toluene (200 g) and the mixture was cooled to 10° C. or less. While continuing the cooling, methanesulfonyl chloride (19.8 g, 0.173 mol) prepared in a dropping funnel was gradually added dropwise thereto. After the completion of the dropwise addition, the reaction was performed at 20° C. for 2 hours. Ethanol (7.97 g, 0.173 mol) was added and the mixture was stirred for a while and filtered, and the organic layer was washed with ion-exchanged water. The organic layer was dried over anhydrous sodium sulfate, and after filtration, the solvent was distilled off under a reduced pressure to obtain a compound of formula (29).

$^1$H-NMR (CDCl$_3$, internal standard TMS); δ (ppm):
1.35 (3H, s, —C$\underline{H}_3$), 1.40 (3H, s, —C$\underline{H}_3$), 1.44-1.83 (6H, m, >CHC$\underline{H}_2$C$\underline{H}_2$C$\underline{H}_2$—), 3.01 (3H, s, —OSO$_2$C$\underline{H}_3$), 3.51 (1H, t, —OC$\underline{H}_2$CH<), 4.03-4.11 (2H, m, —OC$\underline{H}_2$CH<, —OCH$_2$C$\underline{H}$<), 4.24 (2H, t, —C$\underline{H}_2$OSO$_2$CH$_3$)

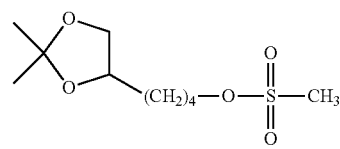

(29)

Example 3

Into a 500 mL four-necked flask equipped with a thermometer, a nitrogen inlet tube, a stirrer and a condenser tube were charged the compound of formula (29) (20.0 g, 79.3 mmol), potassium phthalimide (17.6 g, 95.2 mmol) and dehydrated dimethylformamide (200 g), and the reaction was performed at 60° C. for 2 hours. The mixture was cooled to 10° C. or less, ion-exchanged water (400 g) was added thereto and after stirring for a while, the mixture was extracted with a mixed solution of ethyl acetate/hexane (60/40 in v/v). The organic layer was washed with an aqueous 0.2% by weight potassium carbonate solution and dried over anhydrous sodium sulfate. After filtration, the solvent was distilled off under a reduced pressure to obtain a compound of formula (30).

¹H-NMR (CDCl₃, internal standard TMS); δ (ppm):
1.34 (3H, s, —C$\underline{H}_3$), 1.39 (3H, s, —C$\underline{H}_3$), 1.44-1.75 (6H, m, >CHC$\underline{H}_2$C$\underline{H}_2$C$\underline{H}_2$—), 3.50 (1H, t, —OC$\underline{H}_2$CH<), 3.69 (2H, t, —C$\underline{H}_2$-phthalimide), 4.01-4.09 (2H, m, —OC$\underline{H}_2$CH<, —OC$\underline{H}_2$CH<), 7.71-7.85 (4H, m, -phthalimide)

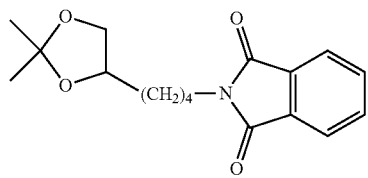

(30)

Example 4

Into a 1 L four-necked flask equipped with a thermometer, a nitrogen inlet tube, a stirrer and a condenser tube were charged the compound of formula (30) (15.2 g, 50.0 mmol), p-toluenesulfonic acid monohydrate (951 mg, 5.00 mmol) and methanol (500 mL), and the reaction was performed at room temperature for 4 hours. Triethylamine (1.01 g, 10.0 mmol) was added thereto and after stirring for a while, the solvent was distilled off under a reduced pressure. The residue was dissolved in chloroform, the solution was washed with ion-exchanged water, and the organic layer was dried over anhydrous sodium sulfate. After filtration, the solvent was distilled off under a reduced pressure to obtain a compound of formula (31).

¹H-NMR (CD₃CN, internal standard TMS); δ (ppm):
1.24-1.61 (6H, m, >CHC$\underline{H}_2$C$\underline{H}_2$C$\underline{H}_2$—), 2.69 (1H, t, —O$\underline{H}$), 2.75 (1H, d, —O$\underline{H}$), 3.17-3.21 (1H, m, —OC$\underline{H}_2$CH<), 3.31-3.37 (1H, m, —OC$\underline{H}_2$CH<), 3.39-3.43 (1H, m, —OCH₂C$\underline{H}$<), 3.54 (2H, t, —C$\underline{H}_2$-phthalimide), 7.67-7.75 (4H, m, -phthalimide)

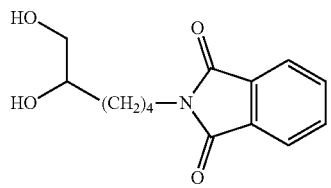

(31)

Example 5

Into a 300 mL three-necked flask equipped with a thermometer, a nitrogen inlet tube, a stirrer, a Dean-stark tube and a condenser tube were charged the compound of formula (31) (3.87 g, 14.7 mmol), 4-hydroxybenzaldehyde (1.20 g, 9.83 mmol), pyridinium p-toluenesulfonate (247 mg, 0.983 mmol) and toluene (180 g), and the reaction was performed for 4 hours while removing by-produced water by azeotropic distillation with toluene. Triethylamine (199 mg, 1.97 mmol) was added thereto and after stirring for a while, the solvent was distilled off under a reduced pressure. The residue was dissolved in chloroform, the solution was washed in order with an aqueous 20% by weight sodium chloride solution and ion-exchanged water, and the organic layer was dried over anhydrous sodium sulfate. After filtra-tion, the solvent was distilled off under a reduced pressure to obtain a compound of formula (32).

¹H-NMR (CDCl₃, internal standard TMS); δ (ppm):
1.41-1.80 (6H, m, >CHC$\underline{H}_2$C$\underline{H}_2$C$\underline{H}_2$—), 3.57-4.26 (5H, m, —OC$\underline{H}_2$C$\underline{H}$<, —C$\underline{H}_2$- phthalimide), 5.71 (0.6H, s, >C$\underline{H}$—), 5.82 (0.4H, s, >C$\underline{H}$—), 6.79-6.82 (2H, m, arom.$\underline{H}$), 7.31-7.35 (2H, m, arom.$\underline{H}$), 7.70-7.86 (4H, m, -phthalimide)

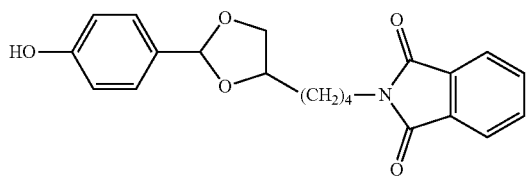

(32)

Example 6

Into a 300 mL four-necked flask equipped with a thermometer, a nitrogen inlet tube, a stirrer and a condenser tube were charged dehydrated methanol (12.8 g, 0.400 mol), dehydrated toluene (150 g) and metal sodium (0.3 g, 13 mmol), and the mixture was stirred at room temperature until the metal sodium was dissolved while bubbling nitrogen through the mixture. The solution was charged into a 5 L autoclave and after the inside of the system was substituted with nitrogen, temperature was raised to 100° C. After adding ethylene oxide (1,987 g, 45 mol) at 100 to 130° C. under a pressure of 1 MPa or less, the reaction was further continued for 2 hours. After the unreacted ethylene oxide gas was removed under a reduced pressure, the mixture was cooled to 60° C. and pH was adjusted to 7.5 with an aqueous 85% phosphoric acid solution to obtain a compound of formula (33).

¹H-NMR (CDCl₃, internal standard TMS); δ (ppm):
2.68 (1H, t, O$\underline{H}$), 3.38 (3H, s, C$\underline{H}_3$O—), 3.49-3.85 (450H, m, —(OC$\underline{H}_2$C$\underline{H}_2$)$_n$—)

GPC analysis;
Number average molecular weight (Mn): 5119, weight average molecular weight (Mw): 5226, polydispersity (Mw/Mn): 1.021

$$CH_3—(OCH_2CH_2)—OH \quad (33)$$

n=about 113

Example 7

Into a 500 mL three-necked flask equipped with a thermometer, a nitrogen inlet tube, a stirrer, a Dean-stark tube and a condenser tube were charged the compound of formula (33) (100 g, 20.0 mmol) and toluene (250 g), and water was removed by azeotropic distillation with toluene. After cooling to 40° C., triethylamine (3.24 g, 32.0 mmol) was charged and methanesulfonyl chloride (2.75 g, 24.0 mmol) prepared in a dropping funnel was gradually added dropwise thereto. After the completion of the dropwise addition, the reaction was performed at 40° C. for 3 hours. Ethanol (1.11 g, 24.0 mmol) was added thereto and the mixture was stirred for a while, filtered, and diluted with ethyl acetate (200 g). Crystallization was performed by adding hexane (500 g), and after filtration, the crystals were dissolved in ethyl acetate (500 g). Crystallization was again performed by adding hexane (500 g), and after filtration, the crystals were dried under a reduced pressure to obtain a compound of formula (34).

$^1$H-NMR (CDCl$_3$, internal standard TMS); δ (ppm):
3.08 (3H, s, —OSO$_2$C$\underline{H}_3$), 3.38 (3H, s, C$\underline{H}_3$O—), 3.52-3.85 (448H, m, —(OC$\underline{H}_2$C$\underline{H}_2$)$_n$—OC$\underline{H}_2$—), 4.37-4.39 (2H, m, —C$\underline{H}_2$OSO$_2$CH$_3$)

GPC analysis;
Number average molecular weight (Mn): 5197, weight average molecular weight (Mw): 5306, polydispersity (Mw/Mn): 1.021

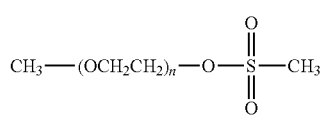

n = about 113

Example 8

Into a 100 mL three-necked flask equipped with a thermometer, a nitrogen inlet tube, a stirrer and a condenser tube were charged the compound of formula (34) (5.00 g, 1.00 mmol), the compound of formula (26) (551 mg, 1.50 mmol), potassium carbonate (691 mg, 5.00 mmol) and acetonitrile (25 g), and the reaction was performed at 80° C. for 4 hours. After distilling off the solvent under a reduce pressure, the residue was dissolved in ethyl acetate (100 g) and the solution was filtered. Crystallization was performed by adding hexane (100 g), and after filtration, the crystals were dried under a reduced pressure to obtain a compound of formula (35).

$^1$H-NMR (CDCl$_3$, internal standard TMS); δ (ppm):
1.40-1.81 (6H, m, >CHC$\underline{H}_2$C$\underline{H}_2$C$\underline{H}_2$—), 3.38 (3H, s, C$\underline{H}_3$O—), 3.52-4.25 (455H, m, —(OC$\underline{H}_2$C$\underline{H}_2$)$_n$—, —OCH$_2$C$\underline{H}$<, —C$\underline{H}_2$-phthalimide), 5.72 (0.6H, s, >C$\underline{H}$—), 5.84 (0.4H, s, >C$\underline{H}$—), 6.89-6.91 (2H, m, arom.$\underline{H}$), 7.35-7.39 (2H, m, arom.$\underline{H}$), 7.70-7.86 (4H, m, -phthalimide) GPC analysis;

Number average molecular weight (Mn): 5462, weight average molecular weight (Mw): 5582, polydispersity (Mw/Mn): 1.022

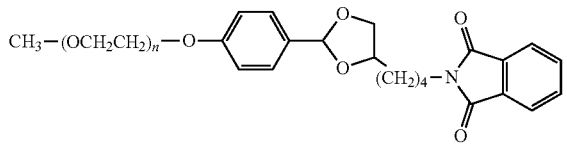

n = about 113

Example 9

Into a 50 mL three-necked flask equipped with a thermometer, a nitrogen inlet tube, a stirrer and a condenser tube were charged the compound of formula (35) (2.00 g, 0.400 mmol), methanol (7 g) and ethylene diamine monohydrate (0.781 g, 10.0 mmol), and the reaction was performed at 40° C. for 4 hours. The mixture was diluted with an aqueous 20% by weight sodium chloride solution, extracted with dichloromethane, and the solvent was distilled off under a reduced pressure. The residue was dissolved in ethyl acetate (50 g), dried over anhydrous sodium sulfate, filtered, and crystallized by adding hexane (50 g). After filtration, the crystals were dried under a reduced pressure to obtain a compound of formula (36).

$^1$H-NMR (CD$_3$OD, internal standard TMS); δ (ppm):
1.43-1.79 (6H, m, >CHC$\underline{H}_2$C$\underline{H}_2$C$\underline{H}_2$—), 2.77 (2H, t, —C$\underline{H}_2$—NH$_2$), 3.36 (3H, s, C$\underline{H}_3$O—), 3.50-4.29 (453H, m, —(OC$\underline{H}_2$C$\underline{H}_2$)$_n$—, —OC$\underline{H}_2$C$\underline{H}$<), 5.70 (0.6H, s, >C$\underline{H}$—), 5.81 (0.4H, s, >C$\underline{H}$—), 6.93-6.98 (2H, m, arom.$\underline{H}$), 7.33-7.41 (2H, m, arom.$\underline{H}$) GPC analysis;

Number average molecular weight (Mn): 5332, weight average molecular weight (Mw): 5454, polydispersity (Mw/Mn): 1.023

n = about 113

Example 10

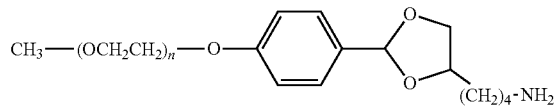

m = about 113

From the compound of formula (37) synthesized according to the method described in JP-A-2010-248504, the tert-butyl group was removed using hydrochloric acid to obtain a compound of formula (38).

$^1$H-NMR (D$_2$O, internal standard TMS); δ (ppm):
3.14 (2H, t, —C$\underline{H}_2$NH$_2$), 3.40-4.00 (452H, m, —(OC$\underline{H}_2$C$\underline{H}_2$)$_m$—)

m=about 113

Example 11

Into a 100 mL three-necked flask equipped with a thermometer, a nitrogen inlet tube, a stirrer and a condenser tube were charged the compound of formula (38) (5.00 g, 1.00 mmol), dichloromethane (30 g) and triethylamine (607 mg, 6.00 mmol), and trifluoroacetic anhydride (630 mg, 3.00 mmol) was added thereto, and the reaction was performed at 25° C. for 3 hours. Phosphate buffer having pH of 7.0 was added thereto and after stirring for a while, the dichloromethane layer was recovered and the solvent was distilled off under a reduced pressure. The residue was dissolved in ethyl acetate (100 g), dried over anhydrous magnesium sulfate, filtered, and crystallized by adding hexane (100 g). After filtration, the crystals were dried under a reduced pressure to obtain a compound of formula (39).

$^1$H-NMR (CDCl$_3$, internal standard TMS); δ (ppm):
2.58 (1H, t, —O$\underline{H}$), 3.40-3.95 (450H, m, —(OC$\underline{H}_2$C$\underline{H}_2$)$_m$—), 7.34 (1H, brs, —$\underline{H}$NCOCF$_3$)

(39)

m = about 113

Example 12

Into a 100 mL three-necked flask equipped with a thermometer, a nitrogen inlet tube, a stirrer and a condenser tube were charged the compound of formula (39) (4.50 g, 0.900 mmol) and dichloromethane (27 g) and N,N'-disuccinimidylcarbonate (692 mg, 2.70 mmol) and triethylamine (410 mg, 4.05 mmol) were added thereto, and the reaction was performed at 25° C. for 4 hours. After filtration, the solvent was distilled off under a reduced pressure. The residue was dissolved in ethyl acetate (90 g) and crystallized by adding hexane (90 g). After filtration, the crystals were dried under a reduced pressure to obtain a compound of formula (40).

$^1$H-NMR (CDCl$_3$, internal standard TMS); δ (ppm):
2.84 (4H, s, -succinimide), 3.40-3.95 (448H, m, —(OC$\underline{H}_2$C$\underline{H}_2$)$_m$—OC$\underline{H}_2$—), 4.44-4.48 (2H, m, —C$\underline{H}_2$O—COO-succinimide), 7.34 (1H, brs, —$\underline{H}$NCOCF$_3$)

GPC analysis;
Number average molecular weight (Mn): 5241, weight average molecular weight (Mw): 5356, polydispersity (Mw/Mn): 1.022

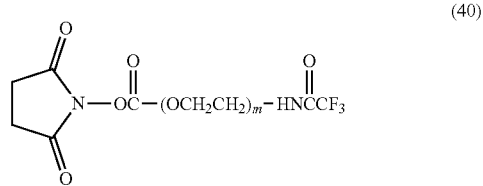

(40)

m = about 113

Example 13

Into a 100 mL three-necked flask equipped with a thermometer, a nitrogen inlet tube, a stirrer and a condenser tube were charged the compound of formula (40) (4.00 g, 0.800 mmol), the compound of formula (36) (4.20 g, 0.840 mmol) and toluene (24 g), and the reaction was performed at 50° C. for 2 hours. Then, Kyoward 700 (1.2 g) was added thereto, and the adsorption treatment was performed at 50° C. for 2 hours. After filtration, crystallization was performed by adding hexane (24 g). After filtration, the crystals were dried under a reduced pressure to obtain a compound of formula (41).

$^1$H-NMR (CDCl$_3$, internal standard TMS); δ (ppm):
1.40-1.81 (6H, m, >CHC$\underline{H}_2$C$\underline{H}_2$C$\underline{H}_2$—), 3.31-3.34 (2H, m, —C$\underline{H}_2$—HNCOO—), 3.38 (3H, s, CH$_3$O—), 3.52-4.25 (903H, m, —(OC$\underline{H}_2$CH$_2$)$_n$—, —(OC$\underline{H}_2$CH$_2$)$_m$—, —OC$\underline{H}_2$C$\underline{H}$<), 5.19 (1H, brs, —$\underline{H}$NCOO—), 5.72 (0.6H, s, >C$\underline{H}$—), 5.84 (0.4H, s, >C$\underline{H}$—), 6.89-6.91 (2H, m, arom.$\underline{H}$), 7.35-7.39 (2H, m, arom.$\underline{H}$), 7.34 (1H, brs, —$\underline{H}$NCOCF$_3$)

GPC analysis;
Number average molecular weight (Mn): 10458, weight average molecular weight (Mw): 11180, polydispersity (Mw/Mn): 1.069

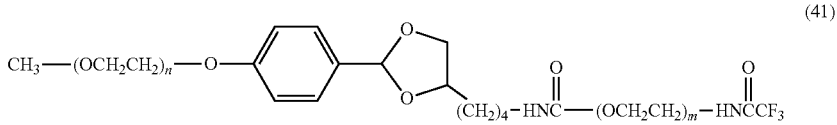

(41)

n = about 113
m = about 113

Example 14

Into a 100 mL three-necked flask equipped with a thermometer, a nitrogen inlet tube, a stirrer and a condenser tube were charged the compound of formula (41) (5.00 g, 0.200 mmol) and 1M aqueous potassium carbonate solution (25 g), and the reaction was performed at 25° C. for 2 hours. The mixture was diluted with an aqueous 20% by weight sodium chloride solution, extracted with dichloromethane, and the solvent was distilled off under a reduced pressure. The residue was dissolved in ethyl acetate (100 g), dried over anhydrous sodium sulfate, filtered, and crystallized by adding hexane (100 g). After filtration, the crystals were dried under a reduced pressure to obtain a compound of formula (42).

$^1$H-NMR (CDCl$_3$, internal standard TMS); δ (ppm):
1.40-1.81 (6H, m, >CHC$\underline{H}_2$C$\underline{H}_2$C$\underline{H}_2$—), 2.86 (2H, t, —C$\underline{H}_2$—NH$_2$), 3.31-3.34 (2H, m, —C$\underline{H}_2$—HNCOO—), 3.38 (3H, s, C$\underline{H}_3$O—), 3.52-4.25 (901H, m, —(OC$\underline{H}_2$CH$_2$)$_n$—, —(OC$\underline{H}_2$CH$_2$)$_m$—OC$\underline{H}_2$—, —OC$\underline{H}_2$C$\underline{H}$<), 5.19 (1H, brs, —$\underline{H}$NCOO—), 5.72 (0.6H, s, >C$\underline{H}$—), 5.84 (0.4H, s, >C$\underline{H}$—), 6.89-6.91 (2H, m, arom.$\underline{H}$), 7.35-7.39 (2H, m, arom.$\underline{H}$)

GPC analysis;
Number average molecular weight (Mn): 10309, weight average molecular weight (Mw): 11021, polydispersity (Mw/Mn): 1.069

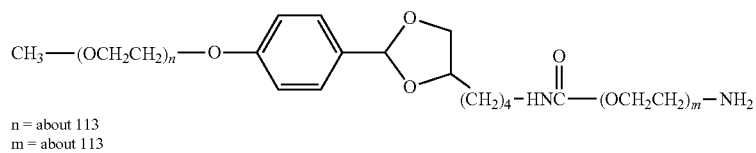

(42)

n = about 113
m = about 113

Example 15

Into a 50 mL three-necked flask equipped with a thermometer, a nitrogen inlet tube, a stirrer and a condenser tube were charged the compound of formula (42) (2.00 g, 0.200 mmol) and toluene (10 g), and N-succinimidyl 3-maleimidopropionate (63.9 mg, 0.240 mmol) was added thereto, and the reaction was performed at 40° C. for 2 hours. After filtration, the mixture was diluted with ethyl acetate (40 g), and crystallized by adding hexane (50 g). After filtration, the crystals were dried under a reduced pressure to obtain a compound of formula (43).

$^1$H-NMR (CDCl$_3$, internal standard TMS); δ (ppm):
1.40-1.81 (6H, m, >CHC<u>H</u>$_2$C<u>H</u>$_2$C<u>H</u>$_2$—), 2.44 (2H, t, —C<u>H</u>$_2$C<u>H</u>$_2$-maleimide), 3.27-3.34 (4H, m, —C<u>H</u>$_2$—HNCOO—, —C<u>H</u>$_2$—NHCOCH$_2$—), 3.38 (3H, s, C<u>H</u>$_3$O—), 3.52-4.25 (903H, m, —(OC<u>H</u>$_2$C<u>H</u>$_2$)$_n$—, —(OC<u>H</u>$_2$C<u>H</u>$_2$)$_m$—OC<u>H</u>$_2$—, —OC<u>H</u>$_2$C<u>H</u><, —C<u>H</u>$_2$C<u>H</u>$_2$-maleimide), 5.19 (1H, brs, —<u>H</u>NCOO—), 5.72 (0.6H, s, >C<u>H</u>—), 5.84 (0.4H, s, >C<u>H</u>—), 6.70 (2H, s, -<u>maleimide</u>), 6.89-6.91 (2H, m, <u>arom.H</u>), 7.35-7.39 (2H, m, <u>arom.H</u>)

GPC analysis;
Number average molecular weight (Mn): 10513, weight average molecular weight (Mw): 11249, polydispersity (Mw/Mn): 1.070

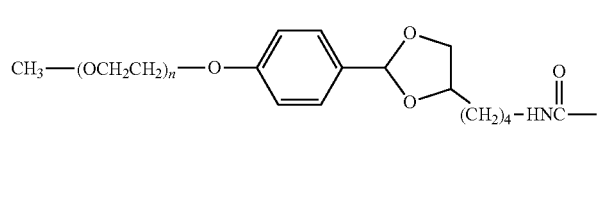

(43)

n = about 113
m = about 113

Example 16

A compound of formula (44) was obtained in the same manner as in Examples 1 to 8 using 3-fluoro-4-hydroxybenzaldehyde.

$^1$H-NMR (CDCl$_3$, internal standard TMS); δ (ppm):
1.38-1.80 (6H, m, >CHC<u>H</u>$_2$C<u>H</u>$_2$C<u>H</u>$_2$—), 3.38 (3H, s, C<u>H</u>$_3$O—), 3.52-4.23 (455H, m, —(OC<u>H</u>$_2$C<u>H</u>$_2$)$_n$—, —OC<u>H</u>$_2$C<u>H</u><, —C<u>H</u>$_2$-phthalimide), 5.70 (0.6H, s, >C<u>H</u>—), 5.82 (0.4H, s, >C<u>H</u>—), 6.95-7.21 (3H, m, <u>arom.H</u>), 7.70-7.86 (4H, m, -<u>phthalimide</u>)

GPC analysis;
Number average molecular weight (Mn): 5485, weight average molecular weight (Mw): 5606, polydispersity (Mw/Mn): 1.022

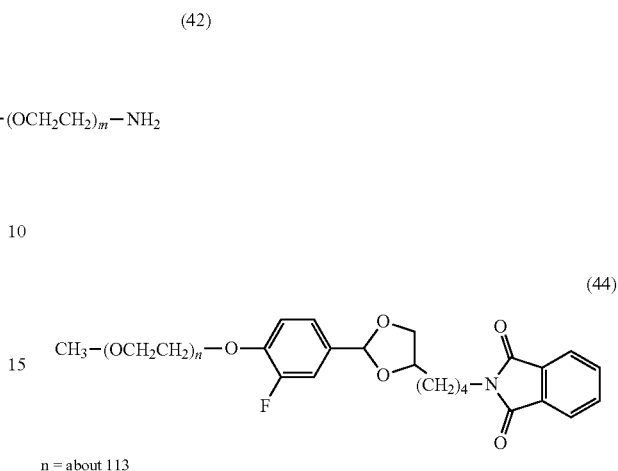

(44)

n = about 113

Example 17

A compound of formula (45) was obtained in the same manner as in Examples 1 to 8 using 2-bromo-5-hydroxybenzaldehyde.

$^1$H-NMR (CDCl$_3$, internal standard TMS); δ (ppm):
1.38-1.80 (6H, m, >CHC<u>H</u>$_2$C<u>H</u>$_2$C<u>H</u>$_2$—), 3.38 (3H, s, C<u>H</u>$_3$O—), 3.52-4.23 (455H, m, —(OC<u>H</u>$_2$C<u>H</u>$_2$)$_n$—, —OC<u>H</u>$_2$C<u>H</u><, —C<u>H</u>$_2$-phthalimide), 5.70 (0.6H, s, >C<u>H</u>—), 5.82 (0.4H, s, >C<u>H</u>—), 6.95-7.21 (3H, m, <u>arom.H</u>), 7.70-7.86 (4H, m, -<u>phthalimide</u>)

GPC analysis;
Number average molecular weight (Mn): 5548, weight average molecular weight (Mw): 5670, polydispersity (Mw/Mn): 1.022

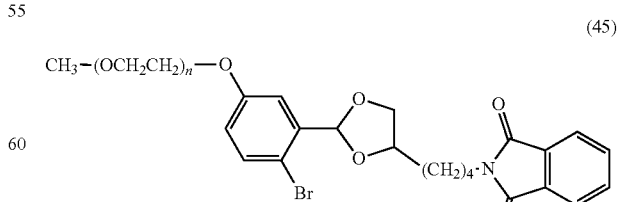

(45)

n = about 113

Example 18

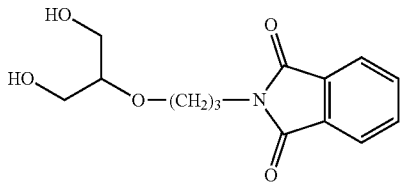
(46)

A compound of formula (46) was synthesized in a manner similar to Examples 1 to 4, and a compound of formula (47) was obtained in the same manner as in Examples 5 to 8 using 3-fluoro-4-hydroxybenzaldehyde.

$^1$H-NMR (CDCl$_3$, internal standard TMS); δ (ppm):

1.89 (2H, m, —CH$_2$CH$_2$-phthalimide), 3.19 (1H, m, —OCH$_2$CH<), 3.38 (3H, s, CH$_3$O—), 3.52-4.41 (456H, m, —(OCH$_2$CH$_2$)$_n$—, —OCH$_2$CH<, —CH$_2$CH$_2$CH$_2$-phthalimide), 5.34 (0.8H, s, >CH—), 5.42 (0.2H, s, >CH—), 6.95-7.25 (3H, m, arom.H), 7.70-7.86 (4H, m, -phthalimide)

GPC analysis;

Number average molecular weight (Mn): 5498, weight average molecular weight (Mw): 5619, polydispersity (Mw/Mn): 1.022

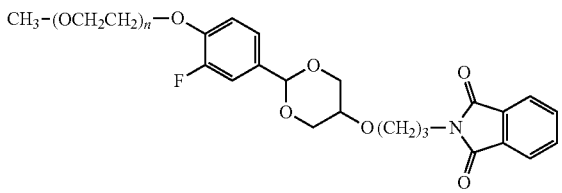
(47)

n = about 113

Example 19

Using the compound of formula (46) and 2-bromo-5-hydroxybenzaldehyde, a compound of formula (48) was obtained in the same manner as in Examples 5 to 8.

$^1$H-NMR (CDCl$_3$, internal standard TMS); δ (ppm):

1.89 (2H, m, —CH$_2$CH$_2$-phthalimide), 3.19 (1H, m, —OCH$_2$CH<), 3.38 (3H, s, CH$_3$O—), 3.52-4.41 (456H, m, —(OCH$_2$CH$_2$)$_n$—, —OCH$_2$CH<, —CH$_2$CH$_2$CH$_2$-phthalimide), 5.61 (0.8H, s, >CH—), 5.68 (0.2H, s, >CH—), 6.78-7.40 (3H, m, arom.H), 7.70-7.86 (4H, m, -phthalimide)

GPC analysis;

Number average molecular weight (Mn): 5564, weight average molecular weight (Mw): 5686, polydispersity (Mw/Mn): 1.022

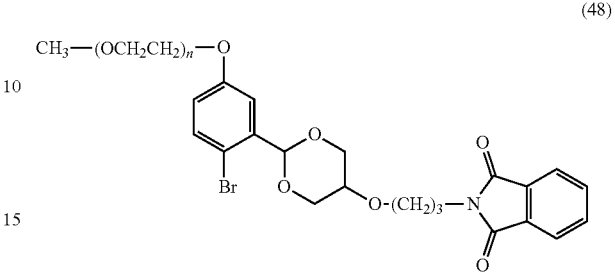
(48)

n = about 113

Example 20

The compound of formula (39) was allowed to react with methanesulfonyl chloride in a manner similar to Example 7 to obtain a compound of formula (49).

$^1$H-NMR (CDCl$_3$, internal standard TMS); δ (ppm):

3.08 (3H, s, —OSO$_2$CH$_3$), 3.40-3.95 (448H, m, —(OCH$_2$CH$_2$)$_m$—OCH$_2$—), 4.37-4.39 (2H, m, —CH$_2$OSO$_2$CH$_3$), 7.34 (1H, brs, —HNCOCF$_3$)

GPC analysis;

Number average molecular weight (Mn): 5193, weight average molecular weight (Mw): 5302, polydispersity (Mw/Mn): 1.021

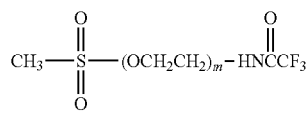
(49)

m = about 113

Example 21

Into a 300 mL three-necked flask equipped with a thermometer, a nitrogen inlet tube, a stirrer, a Dean-stark tube and a condenser tube were charged 1,2,6-hexanetriol (2.01 g, 15.0 mmol), 3-fluoro-4-hydroxybenzaldehyde (1.40 g, 10.0 mmol), p-toluenesulfonic acid monohydrate (19.0 mg, 0.100 mmol) and toluene (183 g), and the reaction was performed for 4 hours while removing by-produced water by azeotropic distillation with toluene. Triethylamine (20.2 mg, 0.200 mmol) was added thereto and after stirring for a while, the solution was washed with an aqueous 10% by weight sodium chloride solution, and the organic layer was dried over anhydrous sodium sulfate. After filtration, the solvent was distilled off under a reduced pressure to obtain a compound of formula (50).

¹H-NMR (CDCl₃, internal standard TMS); δ (ppm):

1.32-1.80 (6H, m, >CHC$\underline{H}$₂C$\underline{H}$₂C$\underline{H}$₂—), 3.50-4.24 (5H, m, —OC$\underline{H}$₂C$\underline{H}$<, —C$\underline{H}$₂—OH), 5.71 (0.6H, s, >C$\underline{H}$—), 5.82 (0.4H, s, >C$\underline{H}$—), 6.73-7.24 (3H, m, arom.$\underline{H}$)

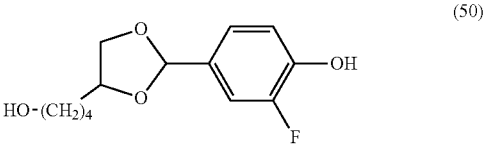
(50)

Example 22

Using the compound of formula (50) and the compound of formula (49), a compound of formula (51) was obtained in the same manner as in Example 8.

¹H-NMR (CDCl₃, internal standard TMS); δ (ppm):

1.40-1.81 (6H, m, >CHC$\underline{H}$₂C$\underline{H}$₂C$\underline{H}$₂—), 3.40-4.25 (455H, m, —(OC$\underline{H}$₂C$\underline{H}$₂)$_m$—, —OC$\underline{H}$₂C$\underline{H}$<, —C$\underline{H}$₂—OH), 5.70 (0.6H, s, >C$\underline{H}$—), 5.82 (0.4H, s, >C$\underline{H}$—), 6.95-7.21 (3H, m, arom.$\underline{H}$), 7.34 (1H, brs, —$\underline{H}$NCOCF₃)

GPC analysis;

Number average molecular weight (Mn): 5239, weight average molecular weight (Mw): 5354, polydispersity (Mw/Mn): 1.022

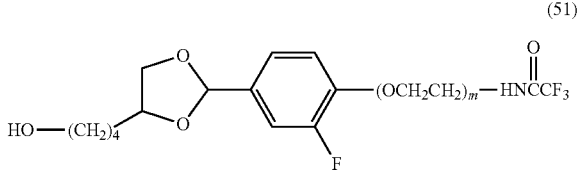
(51)

m = about 113

Example 23

The compound of formula (51) was allowed to react with N,N'-disuccinimidylcarbonate in the same manner as in Example 12 to obtain a compound of formula (52).

¹H-NMR (CDCl₃, internal standard TMS); δ (ppm):

1.40-1.81 (6H, m, >CHC$\underline{H}$₂C$\underline{H}$₂C$\underline{H}$₂—), 2.84 (4H, s, -succinimide), 3.40-4.25 (453H, m, —(OC$\underline{H}$₂C$\underline{H}$₂)$_m$—, —OC$\underline{H}$₂C$\underline{H}$<), 4.33 (2H, dd, —C$\underline{H}$₂O—COO-succinimide), 5.70 (0.6H, s, >C$\underline{H}$—), 5.82 (0.4H, s, >C$\underline{H}$—), 6.95-7.21 (3H, m, arom.$\underline{H}$), 7.34 (1H, brs, —$\underline{H}$NCOCF₃)

GPC analysis;

Number average molecular weight (Mn): 5354, weight average molecular weight (Mw): 5472, polydispersity (Mw/Mn): 1.022

(52)

m = about 113

Example 24

$$CH_3—(OCH_2CH_2)_n—NH_2 \quad (53)$$

n=about 113

Using the compound of formula (53) synthesized according to the method described in JP-A-2010-248504 and the compound of formula (52), a compound of formula (54) was obtained in the same manner as in Example 13.

¹H-NMR (CDCl₃, internal standard TMS); δ (ppm):

1.40-1.81 (6H, m, >CHC$\underline{H}$₂C$\underline{H}$₂C$\underline{H}$₂—), 3.27-3.29 (2H, m, —C$\underline{H}$₂—HNCOO—), 3.38 (3H, s, C$\underline{H}$₃O—), 3.52-4.25 (903H, m, —(OC$\underline{H}$₂C$\underline{H}$₂)$_n$—OC$\underline{H}$₂—, —(OC$\underline{H}$₂C$\underline{H}$₂)$_m$—, —OC$\underline{H}$₂C$\underline{H}$<, —HNCOO—C$\underline{H}$₂—), 5.19 (1H, brs, —$\underline{H}$NCOO—), 5.70 (0.6H, s, >C$\underline{H}$—), 5.82 (0.4H, s, >C$\underline{H}$—), 6.95-7.21 (3H, m, arom.$\underline{H}$), 7.34 (1H, brs, —$\underline{H}$NCOCF₃)

GPC analysis;

Number average molecular weight (Mn): 10138, weight average molecular weight (Mw): 10685, polydispersity (Mw/Mn): 1.054

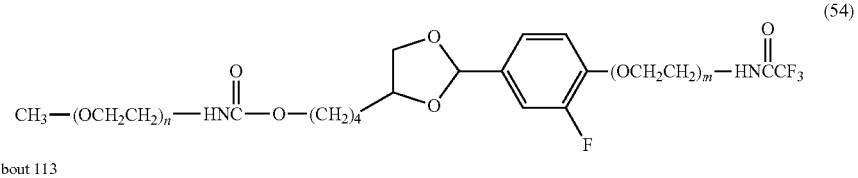
(54)

n = about 113
m = about 113

Example 25

The compound of formula (54) was subjected to deprotection of the trifluoroacetyl group in the same manner as in Example 14, followed by allowing to react with N-succinimidyl 3-maleimidopropionate in the same manner as in Example 15 to obtain a compound of formula (55).

¹H-NMR (CDCl₃, internal standard TMS); δ (ppm):

1.40-1.81 (6H, m, >CHC$\underline{H}$₂C$\underline{H}$₂C$\underline{H}$₂—), 2.44 (2H, t, —C$\underline{H}$₂C$\underline{H}$₂-maleimide), 3.27-3.29 (4H, m, —CH₂—HNCOO—, —CH₂—NHCOCH₂—), 3.38 (3H, s, CH₃O—), 3.52-4.25 (903H, m, —(OCH₂CH₂)ₙ—OCH₂—, —(OCH₂CH₂)ₘ—OCH₂—, —OCH₂CH<, —HNCOO—CH₂—, —CH₂CH₂-maleimide), 5.19 (1H, brs, —HNCOO—), 5.70 (0.6H, s, >CH—), 5.82 (0.4H, s, >CH—), 6.15 (1H, brs, —HNCOCH₂—), 6.70 (2H, s, -maleimide), 6.95-7.21 (3H, m, arom.H)

GPC analysis;

Number average molecular weight (Mn): 10291, weight average molecular weight (Mw): 10847, polydispersity (Mw/Mn): 1.054

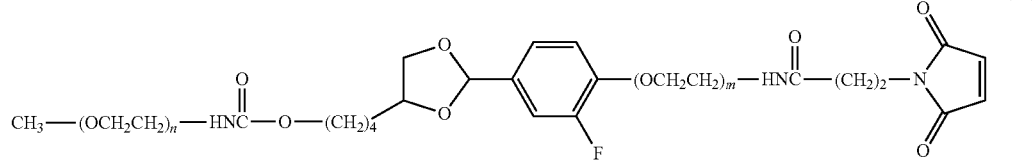

(55)

n = about 113
m = about 113

Example 26

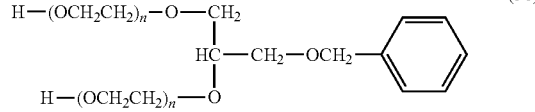

(56)

n = about 113

The compound of formula (56) synthesized according to the method described in JP-A-2004-197077 was allowed to react with acetic anhydride in the presence of triethylamine and 4-dimethylaminopyridine to obtain a compound of formula (57).

¹H-NMR (CDCl₃, internal standard TMS); δ (ppm):

2.08 (6H, s, CH₃CO—), 3.40-4.00 (901H, m, —(OCH₂CH₂)ₙ—OCH₂—, —(OCH₂CH₂)ₙ—OCH<, —CH₂OCH₂Ph), 4.22 (4H, t, CH₃CO₂CH₂—), 4.54 (2H, s, —CH₂OCH₂Ph), 7.27-7.38 (5H, m, —CH₂OCH₂Ph)

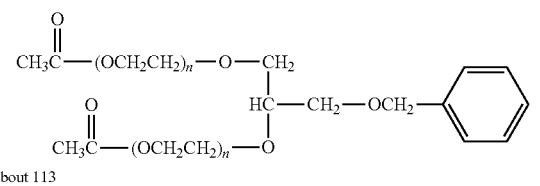

(57)

n = about 113

Example 27

From the compound of formula (57), the benzyl group was removed according to the method described in JP-A-2004-197077, followed by allowing to react with methanesulfonyl chloride in a manner similar to Example 7 to obtain a compound of formula (58).

¹H-NMR (CDCl₃, internal standard TMS); δ (ppm):

2.08 (6H, s, CH₃CO—), 3.08 (3H, s, —OSO₂CH₃), 3.40-4.00 (899H, m, —(OCH₂CH₂)ₙ—OCH₂—, —(OCH₂CH₂)ₙ—OCH<), 4.22 (4H, t, CH₃CO₂CH₂—), 4.26-4.42 (2H, m, —CH₂OSO₂CH₃)

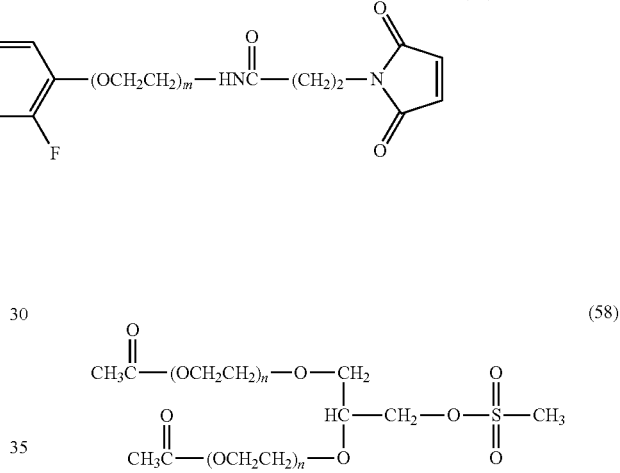

(58)

n = about 113

Example 28

Using 3-fluoro-4-hydroxybenzaldehyde and the compound of formula (58), a compound of formula (59) was obtained in the same manner as in Examples 1 to 5 and 8.

¹H-NMR (CDCl₃, internal standard TMS); δ (ppm):

1.38-1.80 (6H, m, >CHCH₂CH₂CH₂—), 2.08 (6H, s, CH₃CO—), 3.40-4.23 (910H, m, —(OCH₂CH₂)ₙ—OCH₂—, —(OCH₂CH₂)ₙ—OCH<, —OCH₂CH<, —CH₂-phthalimide, CH₃CO₂CH₂—), 5.70 (0.6H, s, >CH—), 5.82 (0.4H, s, >CH—), 6.95-7.21 (3H, m, arom.H), 7.70-7.86 (4H, m, -phthalimide)

GPC analysis;

Number average molecular weight (Mn): 10223, weight average molecular weight (Mw): 10458, polydispersity (Mw/Mn): 1.023

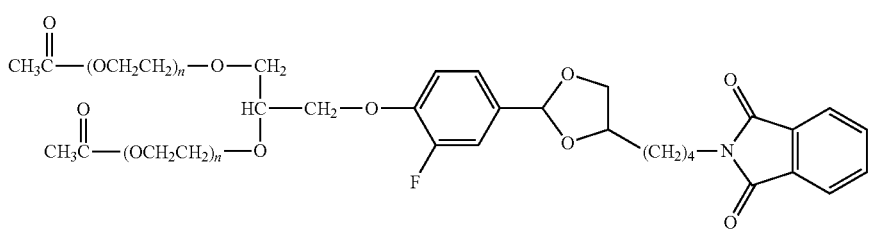

(59)

n = about 113

Example 29

The compound of formula (38) was allowed to react with 5-azidopentanoic anhydride and then allowed to react with N,N'-disuccinimidylcarbonate to obtain a compound of formula (60).

$^1$H-NMR (CDCl$_3$, internal standard TMS); δ (ppm):

1.60-1.74 (4H, m, —CH$_2$C<u>H</u>$_2$C<u>H</u>$_2$CH$_2$N$_3$), 2.18 (2H, t, —C<u>H</u>$_2$CH$_2$CH$_2$CH$_2$N$_3$), 2.84 (4H, s, -<u>succinimide</u>), 3.29 (2H, t, —CH$_2$CH$_2$CH$_2$C<u>H</u>$_2$N$_3$), 3.40-3.85 (448H, m, —(OCH$_2$C<u>H</u>$_2$)$_m$—OC<u>H</u>$_2$—), 4.44-4.48 (2H, m, —CH$_2$O—COO-succinimide), 6.30 (1H, brs, —<u>H</u>NCOCH$_2$—)

GPC analysis;

Number average molecular weight (Mn): 5532, weight average molecular weight (Mw): 5665, polydispersity (Mw/Mn): 1.024

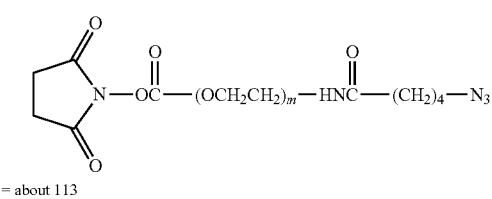

m = about 113

Example 30

A compound of formula (59) was subjected to deprotection of the phthalimide group using ethylene diamine monohydrate and to removal of the acetyl group using an aqueous sodium hydroxide solution, followed by allowing to react with the compound of formula (60) to obtain a compound of formula (61).

$^1$H-NMR (CDCl$_3$, internal standard TMS); δ (ppm):

1.40-1.81 (10H, m, >CHC<u>H</u>$_2$C<u>H</u>$_2$CH$_2$—, —CH$_2$C<u>H</u>$_2$C<u>H</u>$_2$CH$_2$N$_3$), 2.18 (2H, t, —C<u>H</u>$_2$CH$_2$CH$_2$CH$_2$N$_3$), 3.29 (2H, t, —CH$_2$CH$_2$CH$_2$C<u>H</u>$_2$N$_3$), 3.31-3.34 (2H, m, —C<u>H</u>$_2$—HNCOO—), 3.40-4.23 (1353H, m, —(OC<u>H</u>$_2$C<u>H</u>$_2$)$_n$—OC<u>H</u>$_2$—, —(OC<u>H</u>$_2$CH$_2$)$_n$—OC<u>H</u><, —OCH$_2$C<u>H</u><), 5.19 (1H, brs, —<u>H</u>NCOO—), 5.70 (0.6H, s, >C<u>H</u>—), 5.82 (0.4H, s, >C<u>H</u>—), 6.30 (1H, brs, —<u>H</u>NCOCH$_2$—), 6.95-7.21 (3H, m, <u>arom.H</u>)

GPC analysis;

Number average molecular weight (Mn): 14728, weight average molecular weight (Mw): 15582, polydispersity (Mw/Mn): 1.058

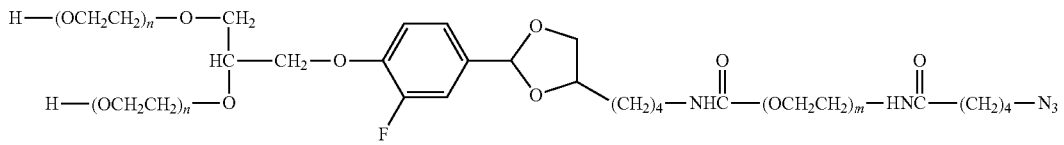

(61)

n = about 113
m = about 113

Example 31

The compound of formula (61) was allowed to react with N,N'-disuccinimidylcarbonate in the same manner as in Example 12 to obtain a compound of formula (62).

$^1$H-NMR (CDCl$_3$, internal standard TMS); δ (ppm):

1.40-1.81 (10H, m, >CHC<u>H</u>$_2$C<u>H</u>$_2$CH$_2$—, —CH$_2$C<u>H</u>$_2$C<u>H</u>$_2$CH$_2$N$_3$), 2.18 (2H, t, —C<u>H</u>$_2$CH$_2$CH$_2$CH$_2$N$_3$), 2.84 (8H, s, -<u>succinimide</u>), 3.29 (2H, t, —CH$_2$CH$_2$CH$_2$C<u>H</u>$_2$N$_3$), 3.31-3.34 (2H, m, —C<u>H</u>$_2$—HNCOO—), 3.40-4.23 (1349H, m, —(OC<u>H</u>$_2$C<u>H</u>$_2$)$_n$—OC<u>H</u>$_2$—, —(OC<u>H</u>$_2$CH$_2$)$_n$—OC<u>H</u><, —OCH$_2$C<u>H</u><), 4.44-4.48 (4H, m, —C<u>H</u>$_2$O—COO-succinimide), 5.19 (1H, brs, —<u>H</u>NCOO—), 5.70 (0.6H, s, >C<u>H</u>—), 5.82 (0.4H, s, >C<u>H</u>—), 6.30 (1H, brs, —<u>H</u>NCOCH$_2$—), 6.95-7.21 (3H, m, <u>arom. H</u>)

GPC analysis;

Number average molecular weight (Mn): 14958, weight average molecular weight (Mw): 15855, polydispersity (Mw/Mn): 1.060

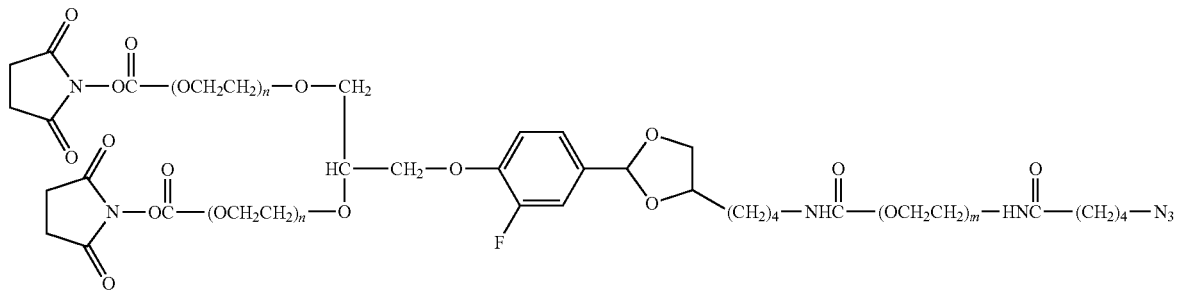

(62)

n = about 113
m = about 113

Example 32

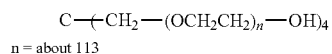

(63)

n = about 113

The compound of formula (63) synthesized by polymerizing ethylene oxide to pentaerythritol was allowed to react with methanesulfonyl chloride in the same manner as in Example 7 to obtain a compound of formula (64).

$^1$H-NMR (CDCl$_3$, internal standard TMS); δ (ppm):
3.08 (12H, s, —OSO$_2$CH$_3$), 3.47-3.85 (1800H, m, —(OCH$_2$CH$_2$)$_n$—OCH$_2$—), 4.37-4.39 (8H, m, —CH$_2$OSO$_2$CH$_3$)

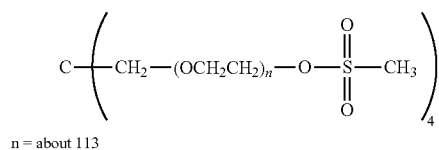

(64)

n = about 113

Example 33

Using the compound of formula (64) and the compound of formula (50), a compound of formula (65) was obtained in the same manner as in Example 8.

$^1$H-NMR (CDCl$_3$, internal standard TMS); δ (ppm):
1.40-1.81 (24H, m, >CHCH$_2$CH$_2$CH$_2$—), 3.52-4.23 (1828H, m, —(OCH$_2$CH$_2$)$_n$—OCH$_2$—, —OCH$_2$CH<, —CH$_2$—OH), 5.70 (2.4H, s, >CH—), 5.82 (1.6H, s, >CH—), 6.95-7.21 (12H, m, arom. H)

GPC analysis;
Number average molecular weight (Mn): 19078, weight average molecular weight (Mw): 19574, polydispersity (Mw/Mn): 1.026

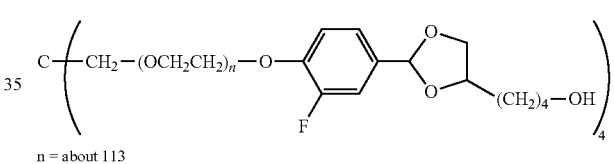

(65)

n = about 113

Example 34

The compound of formula (65) was allowed to react with N,N'-disuccinimidylcarbonate in the same manner as in Example 12 to obtain a compound of formula (66).

$^1$H-NMR (CDCl$_3$, internal standard TMS); δ (ppm):
1.40-1.81 (24H, m, >CHCH$_2$CH$_2$CH$_2$—), 2.84 (16H, s, -succinimide), 3.52-4.23 (1820H, m, —(OCH$_2$CH$_2$)$_n$—OCH$_2$—, —OCH$_2$CH<), 4.33 (8H, dd, —CH$_2$O—COO-succinimide), 5.70 (2.4H, s, >CH—), 5.82 (1.6H, s, >CH—), 6.95-7.21 (12H, m, arom.H)

GPC analysis;
Number average molecular weight (Mn): 19538, weight average molecular weight (Mw): 20046, polydispersity (Mw/Mn): 1.026

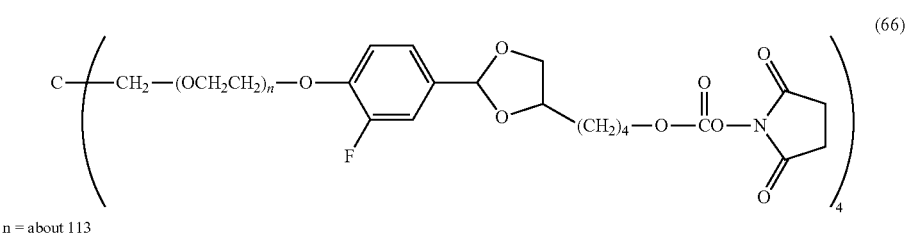

(66)

n = about 113

Example 35

Using the compound of formula (66) and the compound of formula (38), a compound of formula (67) was obtained in the same manner as in Example 13.

$^1$H-NMR (CDCl$_3$, internal standard TMS); δ (ppm):

1.40-1.81 (24H, m, >CHC<u>H</u>$_2$C<u>H</u>$_2$C<u>H</u>$_2$—), 3.27-3.29 (8H, m, —C<u>H</u>$_2$—HNCOO—), 3.52-4.23 (3620H, m, —(OC<u>H</u>$_2$C<u>H</u>$_2$)$_n$—OC<u>H</u>$_2$—, —(OC<u>H</u>$_2$C<u>H</u>$_2$)$_m$—OC<u>H</u>$_2$—, —OC<u>H</u>$_2$C<u>H</u><, —HNCOO—C<u>H</u>$_2$—), 5.19 (4H, brs, —<u>H</u>NCOO—), 5.70 (2.4H, s, >C<u>H</u>—), 5.82 (1.6H, s, >C<u>H</u>—), 6.95-7.21 (12H, m, <u>arom.H</u>)

GPC analysis;

Number average molecular weight (Mn): 37096, weight average molecular weight (Mw): 39878, polydispersity (Mw/Mn): 1.075

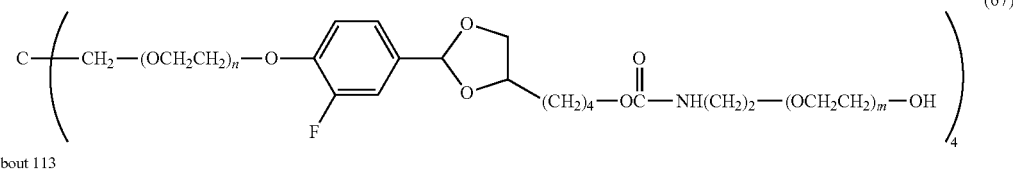

(67)

n = about 113
m = about 113

Example 36

Into a 50 mL three-necked flask equipped with a thermometer, a nitrogen inlet tube and a stirrer were charged the compound of formula (67) (4.00 g, 0.100 mmol) and dichloromethane (20 g), and glutaric anhydride (68.5 mg, 0.600 mmol), triethylamine (60.7 mg, 0.600 mmol) and 4-dimethylaminopyridine (3.7 mg, 0.030 mmol) were added thereto, and the reaction was performed at 25° C. for 6 hours. After filtration, the solvent was distilled off under a reduced pressure. The residue was dissolved in ethyl acetate (100 g) and crystallized by adding hexane (100 g). After filtration, the crystals were dried under a reduced pressure to obtain a compound of formula (68).

$^1$H-NMR (CDCl$_3$, internal standard TMS); δ (ppm):

1.40-1.81 (24H, m, >CHC<u>H</u>$_2$C<u>H</u>$_2$C<u>H</u>$_2$—), 1.97 (8H, quin, —CH$_2$C<u>H</u>$_2$CH$_2$COOH), 2.38-2.46 (16H, m, —C<u>H</u>$_2$CH$_2$C<u>H</u>$_2$COOH), 3.27-3.29 (8H, m, —C<u>H</u>$_2$—HNCOO—), 3.52-4.23 (3620H, m, —(OC<u>H</u>$_2$C<u>H</u>$_2$)$_n$—OC<u>H</u>$_2$—, —(OC<u>H</u>$_2$C<u>H</u>$_2$)$_m$—OC<u>H</u>$_2$—, —OC<u>H</u>$_2$C<u>H</u><, —HNCOO—C<u>H</u>$_2$—, —C<u>H</u>$_2$O—COCH$_2$—), 5.19 (4H, brs, —<u>H</u>NCOO—), 5.70 (2.4H, s, >C<u>H</u>—), 5.82 (1.6H, s, >C<u>H</u>—), 6.95-7.21 (12H, m, <u>arom.H</u>)

GPC analysis;

Number average molecular weight (Mn): 38021, weight average molecular weight (Mw): 40873, polydispersity (Mw/Mn): 1.075

Example 37

A compound of formula (69) was obtained in the same manner as in Example 21 using 4-hydroxybenzaldehyde.

$^1$H-NMR (CDCl$_3$, internal standard TMS); δ (ppm):

1.32-1.80 (6H, m, >CHC<u>H</u>$_2$C<u>H</u>$_2$C<u>H</u>$_2$—), 3.50-4.24 (5H, m, —OC<u>H</u>$_2$C<u>H</u><, —C<u>H</u>$_2$—OH), 5.71 (0.6H, s, >C<u>H</u>—), 5.82 (0.4H, s, >C<u>H</u>—), 6.79-6.82 (2H, m, <u>arom.H</u>), 7.31-7.35 (2H, m, <u>arom.H</u>)

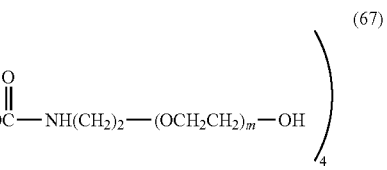

(69)

Example 38

Using the compound of formula (34) and the compound of formula (69), a compound of formula (70) was obtained in the same manner as in Example 8.

$^1$H-NMR (CDCl$_3$, internal standard TMS); δ (ppm):

1.40-1.81 (6H, m, >CHC<u>H</u>$_2$C<u>H</u>$_2$C<u>H</u>$_2$—), 3.38 (3H, s, C<u>H</u>$_3$O—), 3.40-4.25 (455H, m, —(OC<u>H</u>$_2$C<u>H</u>$_2$)$_n$, —OC<u>H</u>$_2$C<u>H</u><, —C<u>H</u>$_2$—OH), 5.72 (0.6H, s, >C<u>H</u>—), 5.84 (0.4H, s, >C<u>H</u>—), 6.89-6.91 (2H, m, <u>arom. H</u>), 7.35-7.39 (2H, m, <u>arom.H</u>)

GPC analysis;

Number average molecular weight (Mn): 5142, weight average molecular weight (Mw): 5255, polydispersity (Mw/Mn): 1.022

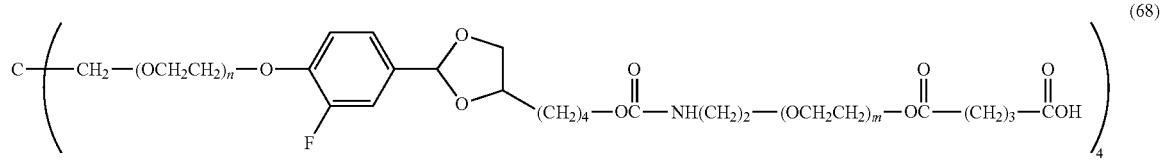

(68)

n = about 113
m = about 113

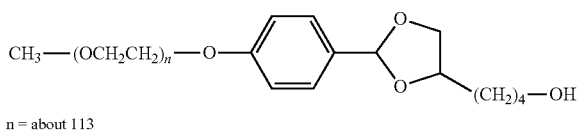

(70)

n = about 113

Example 39

The compound of formula (70) was allowed to react with N,N'-disuccinimidylcarbonate in the same manner as in Example 12 to obtain a compound of formula (71).

$^1$H-NMR (CDCl$_3$, internal standard TMS); δ (ppm):
1.40-1.81 (6H, m, >CHC$\underline{H}_2$C$\underline{H}_2$C$\underline{H}_2$—), 2.84 (4H, s, -succinimide), 3.38 (3H, s, C$\underline{H}_3$O—), 3.40-4.25 (453H, m, —(OC$\underline{H}_2$C$\underline{H}_2$)$_n$, —OC$\underline{H}_2$C$\underline{H}$<), 4.33 (2H, dd, —C$\underline{H}_2$O—COO-succinimide), 5.72 (0.6H, s, >C$\underline{H}$—), 5.84 (0.4H, s, >C$\underline{H}$—), 6.89-6.91 (2H, m, arom.$\underline{H}$), 7.35-7.39 (2H, m, arom. $\underline{H}$)

GPC analysis;
Number average molecular weight (Mn): 5257, weight average molecular weight (Mw): 5373, polydispersity (Mw/Mn): 1.022

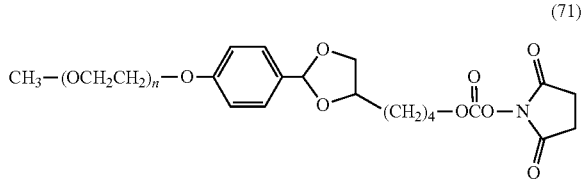

(71)

n = about 113

Example 40

The reaction was performed in the same manner as in Example 8 using the compound of formula (49) and the compound of formula (69) and then the deprotection of trifluoroacetyl group was performed in the same manner as in Example 14 to obtain a compound of formula (72).

$^1$H-NMR (CDCl$_3$, internal standard TMS); δ (ppm):
1.40-1.81 (6H, m, >CHC$\underline{H}_2$C$\underline{H}_2$C$\underline{H}_2$—), 2.86 (2H, t, —C$\underline{H}_2$—NH$_2$), 3.40-4.25 (453H, m, —(OC$\underline{H}_2$C$\underline{H}_2$)$_m$—OC$\underline{H}_2$—, —OC$\underline{H}_2$C$\underline{H}$<, —C$\underline{H}_2$—OH), 5.72 (0.6H, s, >C$\underline{H}$—), 5.84 (0.4H, s, >C$\underline{H}$—), 6.89-6.91 (2H, m, arom.$\underline{H}$), 7.35-7.39 (2H, m, arom.$\underline{H}$)

GPC analysis;
Number average molecular weight (Mn): 5126, weight average molecular weight (Mw): 5239, polydispersity (Mw/Mn): 1.022

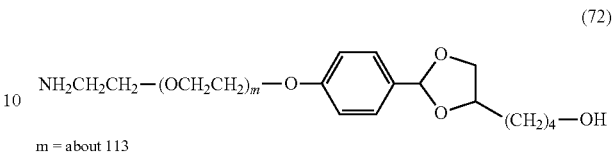

(72)

m = about 113

Example 41

Into a 50 mL three-necked flask equipped with a thermometer, a nitrogen inlet tube, a stirrer and a condenser tube were charged the compound of formula (71) (2.00 g, 0.400 mmol), the compound of formula (72) (2.10 g, 0.420 mmol) and toluene (12 g), and the reaction was performed at 50° C. for 2 hours. Then, Kyoward 200B (0.6 g) was added thereto, and the adsorption treatment was performed at 50° C. for 2 hours. After filtration, crystallization was performed by adding hexane (12 g). After filtration, the crystals were dried under a reduced pressure to obtain a compound of formula (73).

$^1$H-NMR (CDCl$_3$, internal standard TMS); δ (ppm):
1.40-1.81 (12H, m, >CHC$\underline{H}_2$C$\underline{H}_2$C$\underline{H}_2$—), 3.27-3.29 (2H, m, —C$\underline{H}_2$—HNCOO—), 3.38 (3H, s, C$\underline{H}_3$O—), 3.52-4.25 (908H, m, —(OC$\underline{H}_2$C$\underline{H}_2$)$_n$—, —(OC$\underline{H}_2$C$\underline{H}_2$)$_m$—OC$\underline{H}_2$—, —OC$\underline{H}_2$C$\underline{H}$<, —C$\underline{H}_2$—OH, —HNCOO—C$\underline{H}_2$—), 5.72 (1.2H, s, >C$\underline{H}$—), 5.84 (0.8H, s, >C$\underline{H}$—), 6.89-6.91 (4H, m, arom.$\underline{H}$), 7.35-7.39 (4H, m, arom.$\underline{H}$), 7.34 (1H, brs, —$\underline{H}$NCOCF$_3$)

GPC analysis;
Number average molecular weight (Mn): 10268, weight average molecular weight (Mw): 10812, polydispersity (Mw/Mn): 1.053

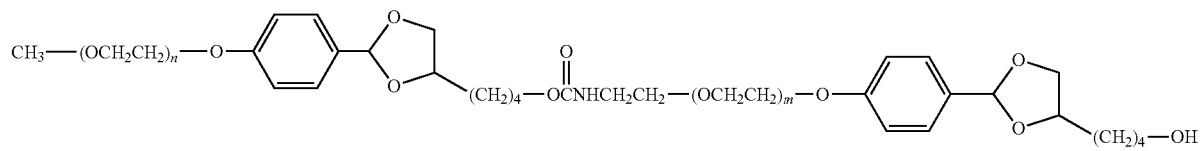

(73)

n = about 113    m = about 113

Example 42

The compound of formula (73) was allowed to react with N,N'-disuccinimidylcarbonate in the same manner as in Example 12 and then the resulting compound was allowed to react with the compound of formula (38) in the same manner as in Example 13 to obtain a compound of formula (74).

$^1$H-NMR (CDCl$_3$, internal standard TMS); δ (ppm):
1.40-1.81 (12H, m, >CHC$\underline{H}_2$C$\underline{H}_2$C$\underline{H}_2$—), 3.27-3.29 (4H, m, —C$\underline{H}_2$—HNCOO—), 3.38 (3H, s, C$\underline{H}_3$O—), 3.52-4.25 (1356H, m, —(OC$\underline{H}_2$C$\underline{H}_2$)$_n$—, —(OC$\underline{H}_2$C$\underline{H}_2$)$_m$—OC$\underline{H}_2$—, —OC$\underline{H}_2$C$\underline{H}$<, —HNCOO—C$\underline{H}_2$—), 5.72 (1.2H, s, >C$\underline{H}$—), 5.84 (0.8H, s, >C$\underline{H}$—), 6.89-6.91 (4H, m, arom.$\underline{H}$), 7.35-7.39 (4H, m, arom.$\underline{H}$), 7.34 (2H, brs, —$\underline{H}$NCOCF$_3$)

GPC analysis;
Number average molecular weight (Mn): 15296, weight average molecular weight (Mw): 16856, polydispersity (Mw/Mn): 1.102

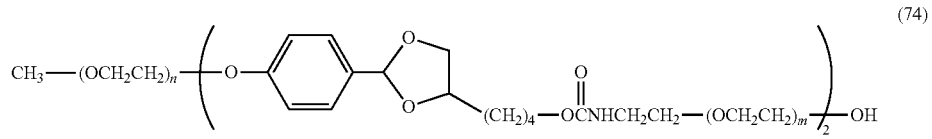

n = about 113   m = about 113

Example 43

The compound of formula (74) was allowed to react with N,N'-disuccinimidylcarbonate in the same manner as in Example 12 to obtain a compound of formula (75).

$^1$H-NMR (CDCl$_3$, internal standard TMS); δ (ppm):
1.40-1.81 (12H, m, >CHC$\underline{H}_2$C$\underline{H}_2$C$\underline{H}_2$—), 2.84 (4H, s, -succinimide), 3.27-3.29 (4H, m, —C$\underline{H}_2$—HNCOO—), 3.38 (3H, s, C$\underline{H}_3$O—), 3.52-4.25 (1354H, m, —(OC$\underline{H}_2$C$\underline{H}_2$)$_n$—, —(OC$\underline{H}_2$CH$_2$)$_m$—OC$\underline{H}_2$—, —OC$\underline{H}_2$C$\underline{H}$<, —HNCOO—C$\underline{H}_2$—), 4.44-4.48 (2H, m, —C$\underline{H}_2$CO—COO-succinimide), 5.72 (1.2H, s, >C$\underline{H}$—), 5.84 (0.8H, s, >C$\underline{H}$—), 6.89-6.91 (4H, m, arom.$\underline{H}$), 7.35-7.39 (4H, m, arom.$\underline{H}$), 7.34 (2H, brs, —$\underline{H}$NCOCF$_3$)

GPC analysis;
Number average molecular weight (Mn): 15439, weight average molecular weight (Mw): 17014, polydispersity (Mw/Mn): 1.102

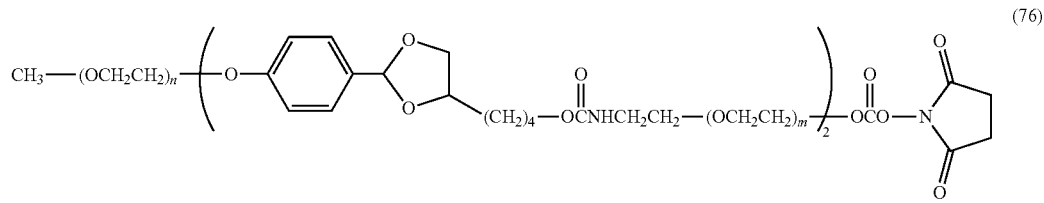

n = about 113   m = about 113

Example 44

A compound of formula (54) was subjected to deprotection of the trifluoroacetyl group in the same manner as in Example 14, followed by allowing to react with the compound of formula (52) in the same manner as in Example 41 to obtain a compound of formula (76).

$^1$H-NMR (CDCl$_3$, internal standard TMS); δ (ppm):
1.40-1.81 (12H, m, >CHC$\underline{H}_2$C$\underline{H}_2$C$\underline{H}_2$—), 3.27-3.29 (4H, m, —C$\underline{H}_2$—HNCOO—), 3.38 (3H, s, C$\underline{H}_3$O—), 3.52-4.25 (1359H, m, —(OC$\underline{H}_2$CH$_2$)$_n$—OC$\underline{H}_2$—, —(OC$\underline{H}_2$C$\underline{H}_2$)$_m$—OC$\underline{H}_2$—, —OC$\underline{H}_2$C$\underline{H}$<, —HNCOO—C$\underline{H}_2$—), 5.19 (2H, brs, —$\underline{H}$NCOO—), 5.70 (1.2H, s, >C$\underline{H}$—), 5.82 (0.8H, s, >C$\underline{H}$—), 6.95-7.21 (6H, m, arom.$\underline{H}$), 7.34 (1H, brs, —$\underline{H}$NCOCF$_3$)

GPC analysis;
Number average molecular weight (Mn): 15279, weight average molecular weight (Mw): 16822, polydispersity (Mw/Mn): 1.101

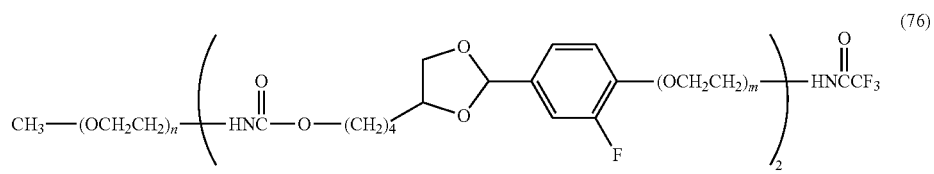

n = about 113   m = about 113

Example 46

A compound of formula (76) was subjected to deprotection of the trifluoroacetyl group in the same manner as in Example 14, followed by allowing to react with N-succinimidyl 3-maleimidopropionate in the same manner as in Example 15 to obtain a compound of formula (77).

$^1$H-NMR (CDCl$_3$, internal standard TMS); δ (ppm):
1.40-1.81 (12H, m, >CHCH$_2$CH$_2$CH$_2$—), 2.44 (2H, t, —CH$_2$CH$_2$-maleimide), 3.27-3.29 (4H, m, —CH$_2$—HNCOO—, —CH$_2$—NHCOCH$_2$—), 3.38 (3H, s, CH$_3$O—), 3.52-4.25 (1359H, m, —(OCH$_2$CH$_2$)$_n$—OCH$_2$—, —(OCH$_2$CH$_2$)$_m$—OCH$_2$—, —OCH$_2$CH<, —HNCOO—CH$_2$—, —CH$_2$CH$_2$-maleimide), 5.19 (2H, brs, —HNCOO—), 5.70 (1.2H, s, >CH—), 5.82 (0.8H, s, >CH—), 6.15 (1H, brs, —HNCOCH$_2$—), 6.70 (2H, s, -maleimide), 6.95-7.21 (6H, m, arom.H)

Figure 4:
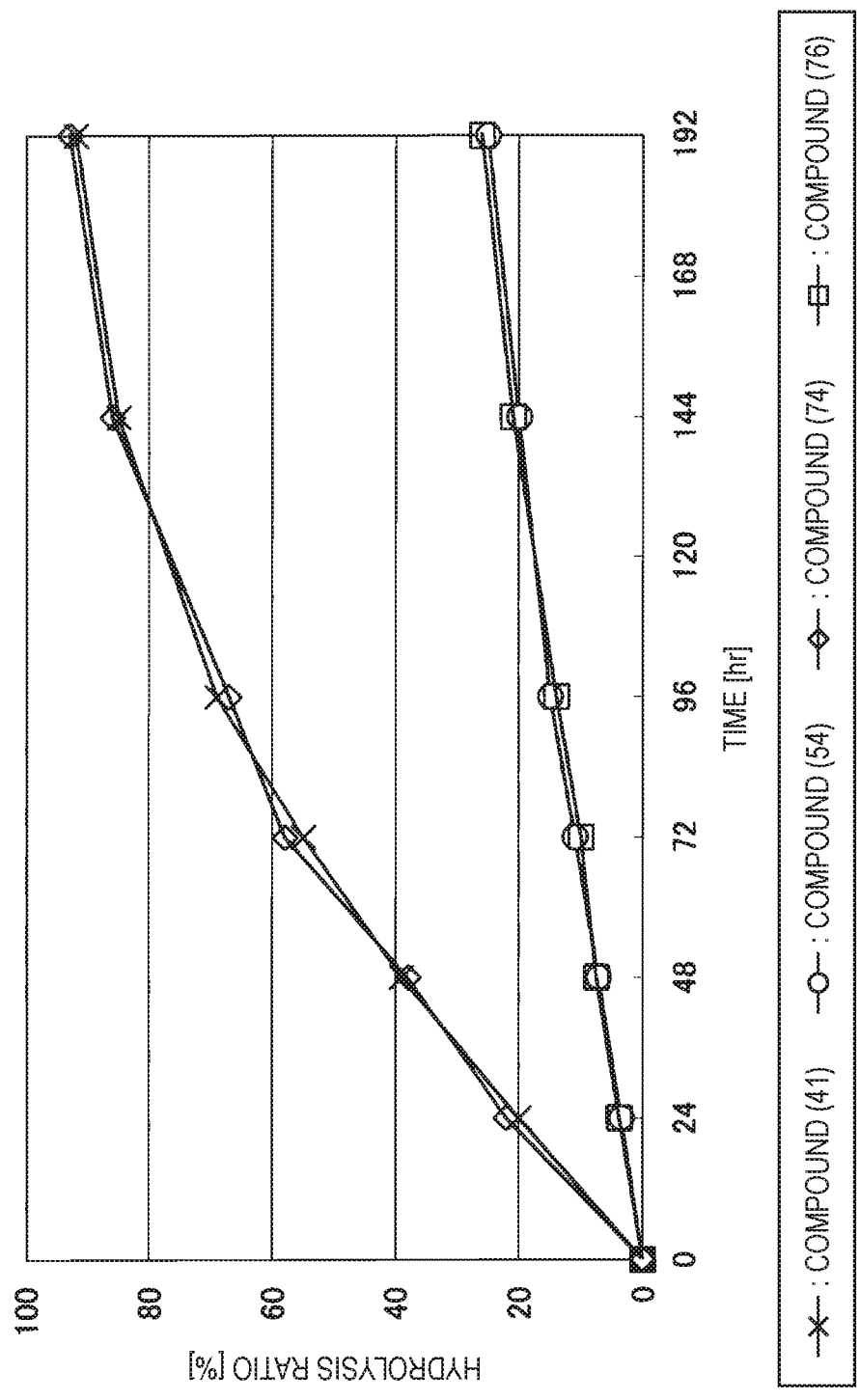
FIG. 4 shows results of the hydrolysis test in HEPES deuterated water buffer of pD 7.4 at 37° C. using the compounds of formula (41), formula (54), formula (74) and formula (76) described in Examples.

GPC analysis;
Number average molecular weight (Mn): 15334, weight average molecular weight (Mw): 16883, polydispersity (Mw/Mn): 1.101 hydrolysis half-lives ($t_{1/2}$) of the compounds of formula (54) and formula (76) in which the structure of the cyclic benzylidene acetal linker was same at pD 5.5 and 37° C. was 12 hours, and was equivalent to the hydrolysis half-life ($t_{1/2}$) of the compound of formula (44) having the same linker structure. As shown in FIG. 4, at pD 7.4 and 37° C., each of the hydrolysis half-lives ($t_{1/2}$) of the compounds of formula (41) and formula (74) was 65 hours, and each of the hydrolysis half-lives ($t_{1/2}$) of the compounds of formula (54) and formula (76) was 18 days, and are equivalent to the hydrolysis half-lives ($t_{1/2}$) of the compound of formula (35) and the compound of formula (44) each having the same linker structure, respectively.

From the above, it was shown that when the structure of the cyclic benzylidene acetal linker was same, the hydrolysis ratio was same, regardless of the number of polyethylene glycols linked.

While the invention has been described in detail and with reference to specific embodiments thereof, it will be apparent to those skilled in the art that various changes and modifications can be made therein without departing from the spirit and scope of the invention.

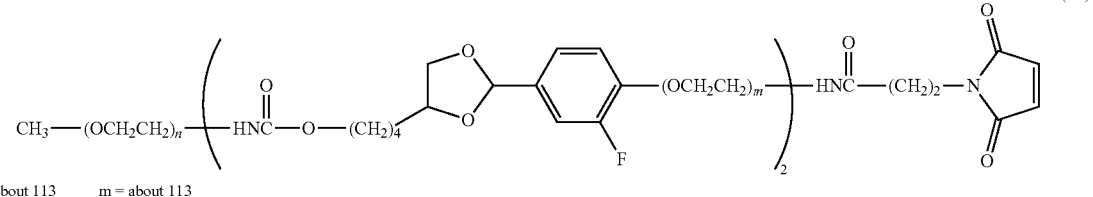

(77)

n = about 113    m = about 113

Example 47

Figure 2:
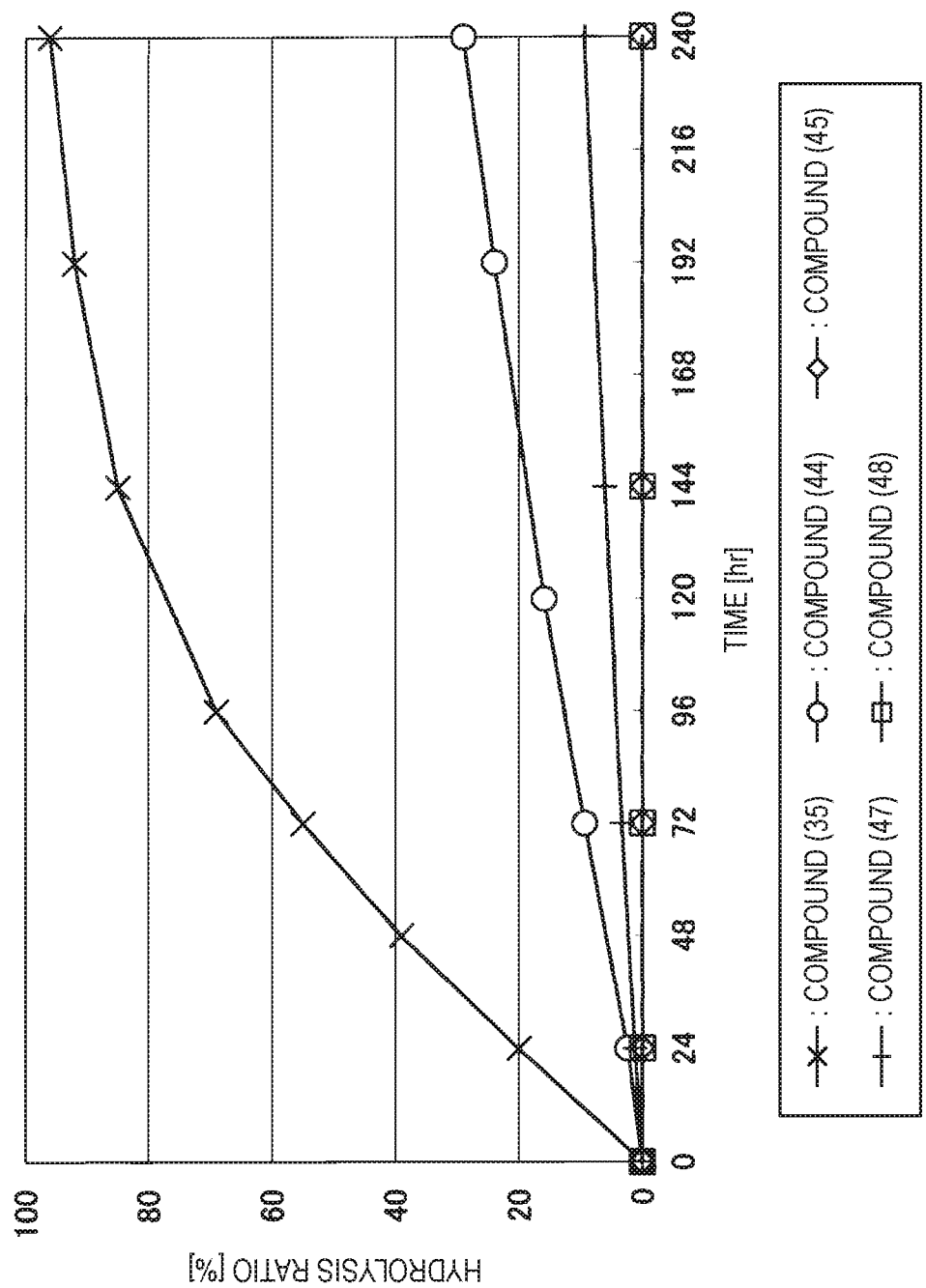
FIG. 2 shows results of the hydrolysis test in HEPES deuterated water buffer of pD 7.4 at 37° C. using the compounds of formula (35), formula (44), formula (45), formula (47) and formula (48) described in Examples.

Each of the compounds (20 mg) of formula (35), formula (44), formula (45), formula (47) and formula (48) was dissolved in MES deuterated water buffer (1 mL) of pD 5.5 and in HEPES deuterated water buffer (1 mL) of pD 7.4, and allowed to stand in a thermostatic bath at 37° C. FIG. 1 and FIG. 2 show the measurement results of hydrolysis rates at pD 5.5 and pD 7.4, respectively.

Figure 3:
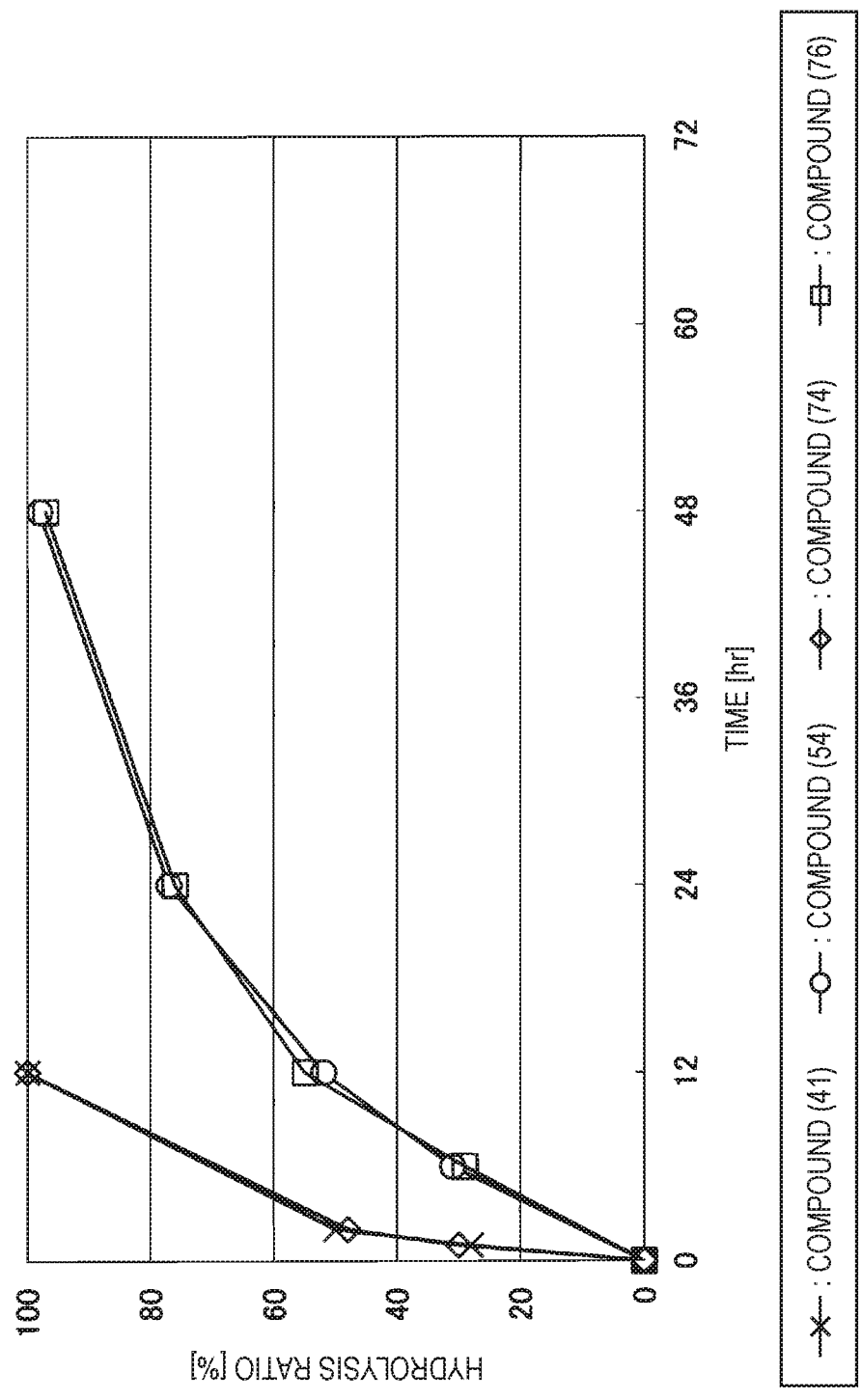
FIG. 3 shows results of the hydrolysis test in MES deuterated water buffer of pD 5.5 at 37° C. using the compounds of formula (41), formula (54), formula (74) and formula (76) described in Examples.

Each of the compounds (200 mg) of formula (41), formula (54), formula (74) and formula (76) was dissolved in MES deuterated water buffer (10 mL) of pD 5.5 and in HEPES deuterated water buffer (10 mL) of pD 7.4, and allowed to stand in a thermostatic bath at 37° C. FIG. 3 and FIG. 4 show the measurement results of hydrolysis rates at pD 5.5 and pD 7.4, respectively.

As shown in FIG. 1, the hydrolysis half-lives ($t_{1/2}$) of the compounds of formula (35), formula (44), formula (45), formula (47) and formula (48) at pD 5.5 and 37° C. were 2 hours, 12 hours, 30 days, 24 hours and 6 months, respectively. Further, as shown in FIG. 2, at pD 7.4 and 37° C., the hydrolysis half-lives ($t_{1/2}$) of the compounds of formula (35) and formula (44) were 65 hours and 18 days, respectively, the hydrolysis of approximately 17% was observed for 18 days for the compound of formula (47), and no hydrolysis was observed even after 18 days for the compounds of formula (45) and formula (48).

As shown in FIG. 3, any of the hydrolysis half-lives ($t_{1/2}$) of the compounds of formula (41) and formula (74) in which the structure of the cyclic benzylidene acetal linker was same at pD 5.5 and 37° C. was 2 hours, and was equivalent to the hydrolysis half-life ($t_{1/2}$) of the compound of formula (35) having the same linker structure. Further, any of the This application is based on a Japanese patent application filed on Mar. 31, 2015 (Japanese Patent Application No. 2015-070659, and the whole contents thereof are incorporated herein by reference. Also, all the references cited herein are incorporated as a whole.

The invention claimed is:

1. A method for chemical modification of a biofunctional molecule with a biodegradable polyethylene glycol compound having a cyclic benzylidene acetal linker for improving in vivo and intracellular kinetics in environments having different pH in a living body, which comprises reacting a functional group in the biofunctional molecule with a chemically reactive functional group in the biodegradable polyethylene glycol compound having a cyclic benzylidene acetal linker, wherein the biodegradable polyethylene glycol compound having a cyclic benzylidene acetal linker is represented by formula (1) or formula (2):

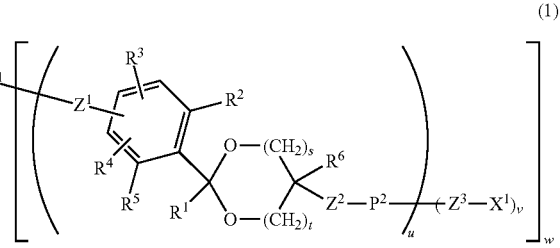

(1)

-continued

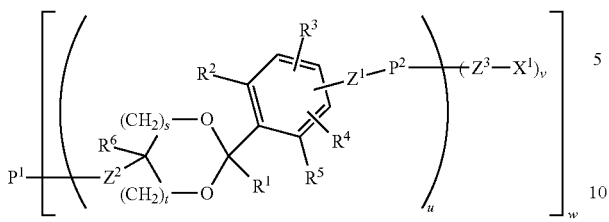

(2)

wherein, in the formula (1) and the formula (2), $R^1$ and $R^6$ are each independently a hydrogen atom or a hydrocarbon group;

$R^2$, $R^3$, $R^4$ and $R^5$ are each independently an electron-withdrawing or electron-donating substituent or a hydrogen atom;

s is 1 or 2, t is 0 or 1, and s+t is 1 or 2;

$P^1$ is a straight-chain or branched polyethylene glycol having a number of ethylene glycol units of 3 or more;

$P^2$ is a straight-chain or branched polyethylene glycol having a number of ethylene glycol units of 3 or more;

w is an integer of 1 to 8;

u is an integer of 1 to 40;

v is an integer of 1 to 4;

$X^1$ is the chemically reactive functional group and is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group; and $Z^1$, $Z^2$ and $Z^3$ are each independently a selected divalent spacer.

2. The method as claimed in claim 1, wherein s is 1 and t is 0, and $R^2$ and $R^5$ are each a hydrogen atom, wherein the electron-withdrawing substituent is selected from the group consisting of an acyl group having from 2 to 5 carbon atoms, an alkoxycarbonyl group having from 2 to 5 carbon atoms, a carbamoyl group having from 2 to 5 carbon atoms, an acyloxy group having from 2 to 5 carbon atoms, an acylamino group having from 2 to 5 carbon atoms, an alkoxycarbonylamino group having from 2 to 5 carbon atoms, a fluorine atom, a chlorine atom, a bromine atom, an iodine atom, an alkylsulfanyl group having from 1 to 4 carbon atoms, an alkylsulfonyl group having from 1 to 4 carbon atoms, an arylsulfonyl group having from 6 to 10 carbon atoms, a nitro group, a trifluoromethyl group and a cyano group, and the electron-donating substituent is selected from the group consisting of an alkyl group having from 1 to 4 carbon atoms, an alkoxy group having from 1 to 4 carbon atoms, an aryl group having from 6 to 10 carbon atom and an aryloxy group having from 6 to 10 carbon atoms.

3. The method as claimed in claim 1, wherein s is 1 and t is 0, and at least one of $R^2$ and $R^5$ is an electron-withdrawing or electron-donating substituent, wherein the electron-withdrawing substituent is selected from the group consisting of an acyl group having from 2 to 5 carbon atoms, an alkoxycarbonyl group having from 2 to 5 carbon atoms, a carbamoyl group having from 2 to 5 carbon atoms, an acyloxy group having from 2 to 5 carbon atoms, an acylamino group having from 2 to 5 carbon atoms, an alkoxycarbonylamino group having from 2 to 5 carbon atoms, a fluorine atom, a chlorine atom, a bromine atom, an iodine atom, an alkylsulfanyl group having from 1 to 4 carbon atoms, an alkylsulfonyl group having from 1 to 4 carbon atoms, an arylsulfonyl group having from 6 to 10 carbon atoms, a nitro group, a trifluoromethyl group and a cyano group, and the electron-donating substituent is selected from the group consisting of an alkyl group having from 1 to 4 carbon atoms, an alkoxy group having from 1 to 4 carbon atoms, an aryl group having from 6 to 10 carbon atom and an aryloxy group having from 6 to 10 carbon atoms.

4. The method as claimed in claim 1, wherein s is 1 and t is 1, or s is 2 and t is 0, and $R^2$ and $R^5$ are each a hydrogen atom.

5. The method as claimed in claim 1, wherein s is 1 and t is 1, or s is 2 and t is 0, and at least one of $R^2$ and $R^5$ is an electron-withdrawing or electron-donating substituent.

6. The method as claimed in claim 1, wherein w is 1.

7. The method as claimed in claim 6, wherein $P^1$ is a straight-chain polyethylene glycol having a hydrocarbon group or a chemically reactive functional group at a terminal thereof, wherein the chemically reactive functional group is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

8. The method as claimed in claim 7, wherein $P^1$ is represented by formula (3):

wherein, in the formula (3), Y is a hydrocarbon group having from 1 to 24 carbon atoms; and n is an integer of 3 to 2,000.

9. The method as claimed in claim 7, wherein $P^1$ is represented by formula (4):

wherein, in the formula (4), $X^2$ is a chemically reactive functional group different from $X^1$; $Z^4$ is a divalent spacer; and n is an integer of 3 to 2,000.

10. The method as claimed in claim 6, wherein $P^1$ is a branched polyethylene glycol having a hydrocarbon group or a chemically reactive functional group different from $X^1$ at a terminal thereof.

11. The method as claimed in claim 10, wherein $P^1$ is represented by formula (5):

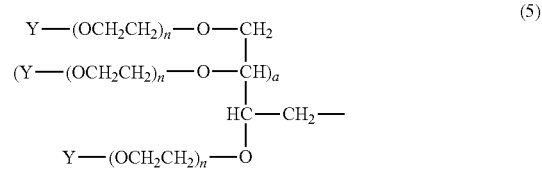

wherein, in the formula (5), Y is a hydrocarbon group having from 1 to 24 carbon atoms; n is an integer of 3 to 1,000; and a is 0 or 2.

12. The method as claimed in claim 10, wherein P¹ is represented by formula (6):

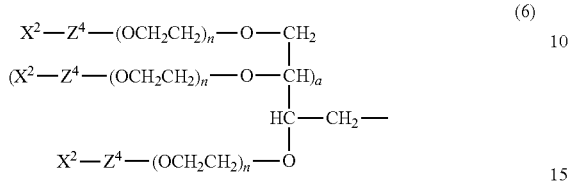

wherein, in the formula (6), X² is a chemically reactive functional group different from X¹; Z⁴ is a divalent spacer; n is an integer of 3 to 1,000, and a is 0 or 2.

13. The method as claimed in claim 1, wherein w is 2 to 8.

14. The method as claimed in claim 13, wherein P¹ is represented by formula (7):

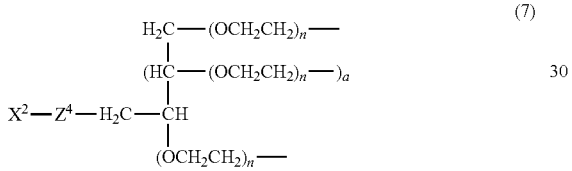

wherein, in the formula (7), X² is a chemically reactive functional group different from X¹; Z⁴ is a divalent spacer; n is an integer of 3 to 1,000, and a is 0 or 2.

15. The method as claimed in claim 13, wherein P¹ is a straight-chain polyethylene glycol or a branched polyethylene glycol having a number of terminals of 3 to 8, all terminals of the polyethylene glycol constituting P¹ are each connected to Z¹ in formula (1) or Z² in formula (2), and w is equal to the number of terminals of the polyethylene glycol.

16. The method as claimed in claim 15, wherein P¹ is selected from the group consisting of formula (r), formula (s), formula (t), formula (u) and formula (v):

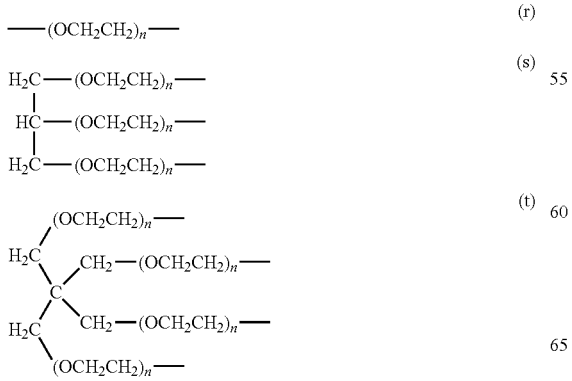

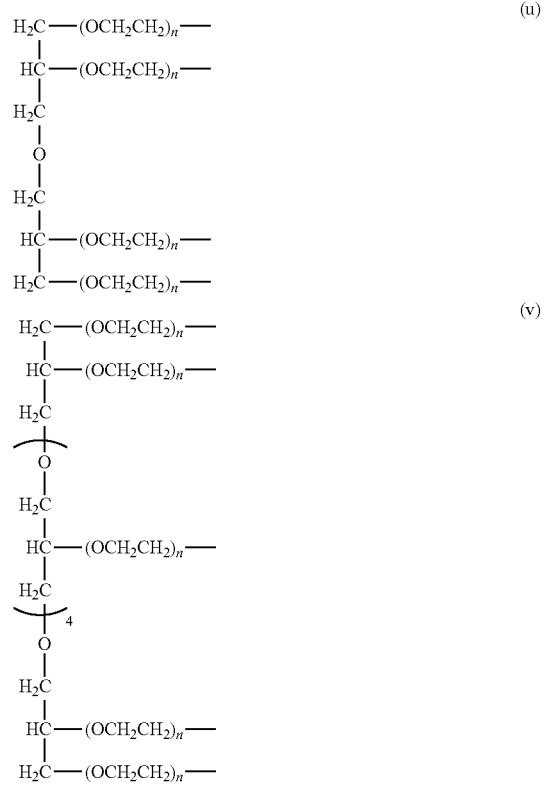

wherein, in the formulae, n is an integer of 3 to 2,000; and w is 2 in a case where P¹ is represented by formula (r), w is 3 in a case where P¹ is represented by formula (s), w is 4 in a case where P¹ is represented by formula (t), w is 4 in a case where P¹ is represented by formula (u), and w is 8 in a case where P¹ is represented by formula (v).

17. The method as claimed in claim 1, wherein P² is represented by formula (8):

wherein, in the formula (8), m is an integer of 3 to 2,000; and v in formula (1) or formula (2) is 1.

18. The method as claimed in claim 1, wherein P² is represented by formula (9):

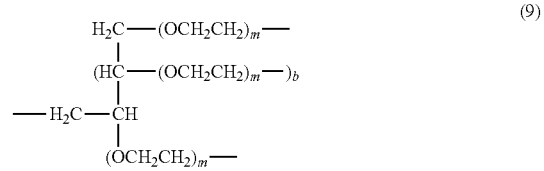

wherein, in the formula (9), m is an integer of 3 to 1,000, b is 0 or 2; and v in formula (1) or formula (2) is b+2.

19. The method as claimed in claim 1, wherein Z¹, Z² and Z³ are each independently an ether bond, an ester bond, a carbonate bond, a urethane bond, an amide bond, a secondary amino group, an alkylene group containing any of these bonds and group, a single bond or an alkylene group.

20. The method as claimed in claim 9, wherein X² is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

21. The method as claimed in claim 9, wherein $Z^4$ is an ether bond, an ester bond, a carbonate bond, a urethane bond, an amide bond, a secondary amino group, an alkylene group containing any of these bonds and group, a single bond or an alkylene group.

* * * * *